US011517284B2

(12) United States Patent
Seki et al.

(10) Patent No.: US 11,517,284 B2
(45) Date of Patent: Dec. 6, 2022

(54) ULTRASOUND IMAGING APPARATUS WITH BANK TANK

(71) Applicant: Lily MedTech Inc., Tokyo (JP)

(72) Inventors: Mika Seki, Tokyo (JP); Kazuo Yuge, Tokyo (JP); Yu Takamura, Takamura (JP)

(73) Assignee: Lily MedTech Inc., Tokyo (JP)

( * ) Notice: Subject to any disclaimer, the term of this patent is extended or adjusted under 35 U.S.C. 154(b) by 0 days.

(21) Appl. No.: 16/652,249

(22) PCT Filed: Oct. 2, 2018

(86) PCT No.: PCT/JP2018/036823
§ 371 (c)(1),
(2) Date: Mar. 30, 2020

(87) PCT Pub. No.: WO2019/069898
PCT Pub. Date: Apr. 11, 2019

(65) Prior Publication Data
US 2020/0237322 A1    Jul. 30, 2020

(30) Foreign Application Priority Data

Oct. 2, 2017 (JP) .............................. JP2017-192802

(51) Int. Cl.
*A61B 8/08* (2006.01)
*G01S 15/89* (2006.01)
(Continued)

(52) U.S. Cl.
CPC ............ *A61B 8/0825* (2013.01); *A61B 8/406* (2013.01); *A61B 8/4461* (2013.01);
(Continued)

(58) Field of Classification Search
CPC ..... A61B 8/0825; A61B 8/406; A61B 8/4461; A61B 8/5276; A61B 8/54; A61B 8/5223;
(Continued)

(56) References Cited

U.S. PATENT DOCUMENTS 8,496,586 B2 *  7/2013  Zhang .................... A61B 8/463
                                                            600/437
8,876,716 B2    11/2014  Duric et al.
(Continued)

FOREIGN PATENT DOCUMENTS

JP    2013519455 A    5/2013
JP    2014121434 A    7/2014
(Continued)

OTHER PUBLICATIONS

Duric et al., "In-vivo imaging results with ultrasound tomography: Report on an ongoing study at the Karmanos Cancer Institute", Proc. of Spie, 2010, 9 pages, vol. 7629.
(Continued)

*Primary Examiner* — Joel Lamprecht
*Assistant Examiner* — Nyrobi Celestine
(74) *Attorney, Agent, or Firm* — The Webb Law Firm

(57) ABSTRACT

The medical imaging apparatus of the present invention includes a bath tank for accommodating a test subject, the test subject being at least a portion of a body of a human subject; a measurement device movable in a predetermined direction, the measurement device including ab group of elements to emit a radiation wave into the bath tank and receive a scattered radiation wave; and a control unit for measuring by the measurement device when at least one of a location of the test subject within a plane orthogonal to the predetermined direction, a location of the test subject in the predetermined direction, and continuity of data measured by the measurement device satisfies a predetermined condition.

(Continued)

Because of this configuration, the medical imaging apparatus is able to acquire data covering the entire measurement target site.

8 Claims, 18 Drawing Sheets

(51) Int. Cl.
 *A61B 8/00* (2006.01)
 *G06T 7/00* (2017.01)
(52) U.S. Cl.
 CPC .......... *A61B 8/4483* (2013.01); *A61B 8/5207* (2013.01); *A61B 8/5276* (2013.01); *A61B 8/54* (2013.01); *G01S 15/8922* (2013.01); *G01S 15/8945* (2013.01); *A61B 8/0858* (2013.01); *A61B 8/4438* (2013.01); *A61B 8/467* (2013.01); *A61B 8/5223* (2013.01); *G06T 7/0012* (2013.01)
(58) Field of Classification Search
 CPC ..... A61B 8/0858; A61B 5/708; A61B 6/0435; A61B 6/502; A61B 5/0091; G01S 15/8945
 See application file for complete search history.

(56) References Cited

U.S. PATENT DOCUMENTS

| | | | |
|---|---|---|---|
| 10,074,199 B2* | 9/2018 | Robinson | .............. G06T 11/005 |
| 10,650,518 B2* | 5/2020 | Ryu | ........................ G16H 50/30 |
| 2007/0133736 A1* | 6/2007 | Chen | ........................ A61B 6/00 |
| | | | 378/5 |
| 2008/0234578 A1* | 9/2008 | Claus | ........................ G06T 7/38 |
| | | | 600/437 |
| 2008/0319317 A1* | 12/2008 | Kamiyama | ............. A61B 8/463 |
| | | | 600/443 |
| 2009/0198128 A1* | 8/2009 | Fukutani | .............. A61B 8/0825 |
| | | | 600/437 |
| 2009/0204007 A1* | 8/2009 | Katoh | ................... A61B 8/0858 |
| | | | 600/463 |
| 2009/0306505 A1 | 12/2009 | Yoshikawa et al. | |
| 2010/0240992 A1* | 9/2010 | Hao | ........................ A61B 8/585 |
| | | | 600/437 |
| 2012/0029358 A1 | 2/2012 | Lin | |
| 2012/0277574 A1* | 11/2012 | Panescu | ................... A61B 5/06 |
| | | | 600/421 |
| 2013/0123627 A1* | 5/2013 | Oyama | ................... A61B 8/483 |
| | | | 600/442 |
| 2013/0310692 A1* | 11/2013 | Watson | ................ A61B 8/4461 |
| | | | 600/452 |
| 2015/0221091 A1* | 8/2015 | Sugiyama | ............ A61B 8/5261 |
| | | | 382/131 |
| 2015/0366535 A1 | 12/2015 | Eggers et al. | |
| 2016/0331347 A1* | 11/2016 | Ebisawa | ................ A61B 8/406 |
| 2017/0055844 A1 | 3/2017 | Umezawa et al. | |
| 2017/0143304 A1 | 5/2017 | Malik et al. | |
| 2017/0281125 A1* | 10/2017 | Furukawa | ................ A61B 8/14 |
| 2017/0347889 A1* | 12/2017 | Yamamoto | .......... G01S 15/8965 |
| 2018/0132722 A1* | 5/2018 | Eggers | ................. A61B 8/4254 |
| 2020/0196971 A1* | 6/2020 | Laviola | ................. A61B 6/465 |

FOREIGN PATENT DOCUMENTS

| | | | |
|---|---|---|---|
| KR | 20120057782 A | * | 6/2012 |
| WO | 03101303 A1 | | 12/2003 |

OTHER PUBLICATIONS

Ruiter et al., "First Results of a Clinical Study with 3D Ultrasound Computer Tomography", IEEE, 2013, pp. 651-654.

* cited by examiner

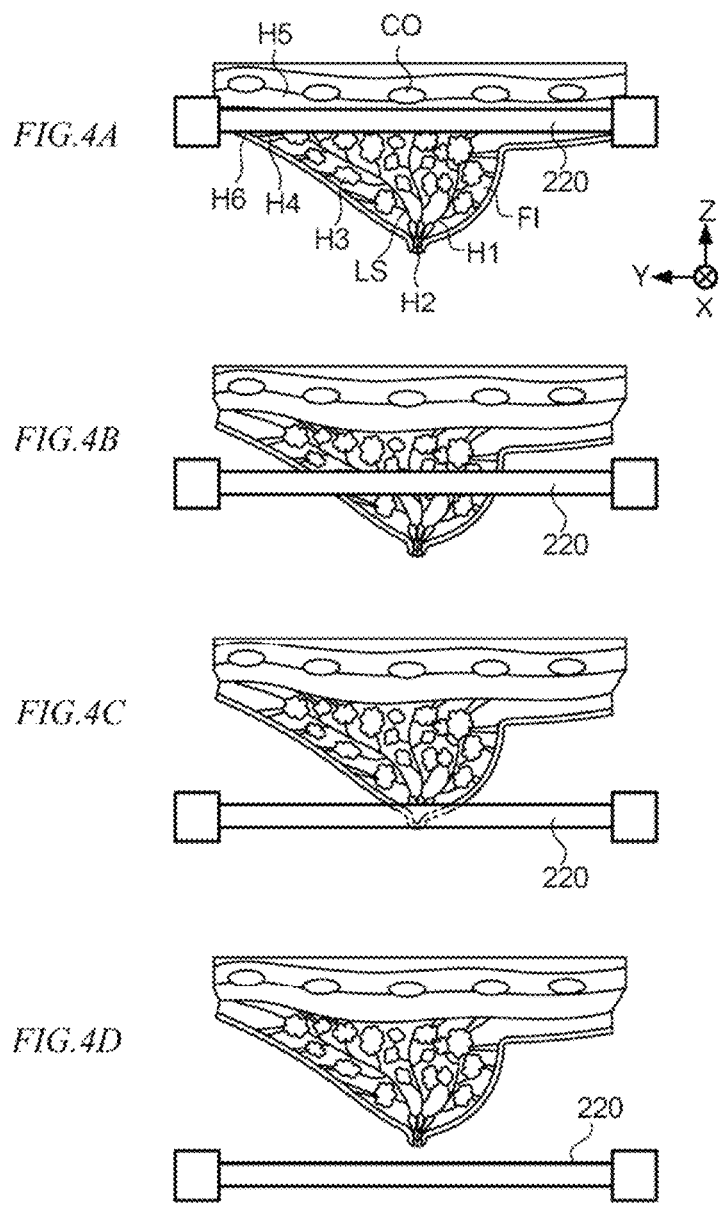

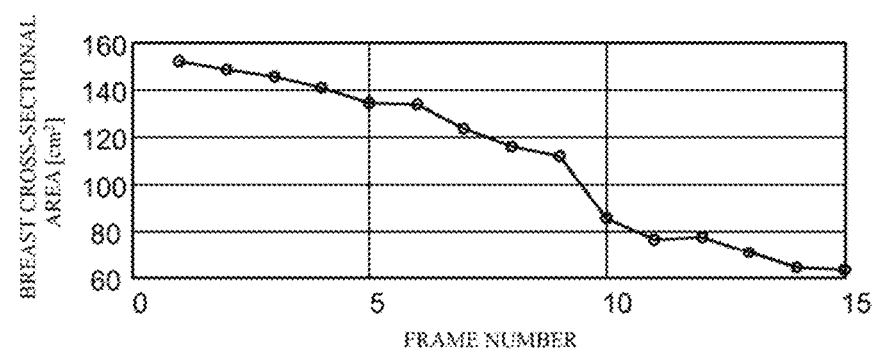
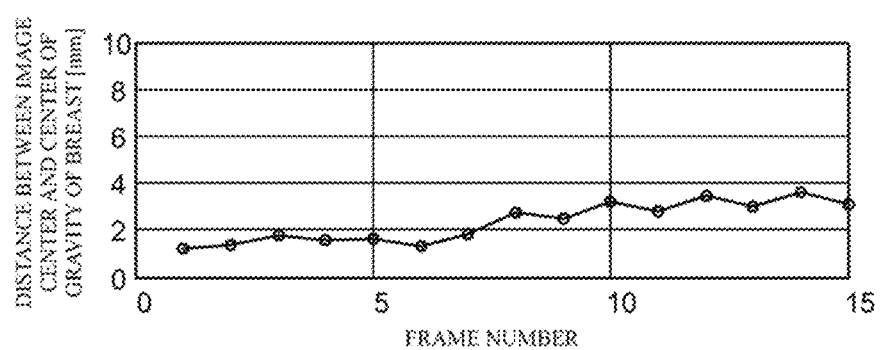
*FIG.8C*

ULTRASOUND IMAGING APPARATUS WITH BANK TANK

CROSS-REFERENCE TO RELATED APPLICATIONS

This application is the United States national phase of International Application No. PCT/JP2018/036823 filed Oct. 2, 2018, and claims priority to Japanese Patent Application No. 2017-192802 filed Oct. 2, 2017, the disclosures of which are hereby incorporated by reference in their entirety.

TECHNICAL FIELD

The present invention relates to a medical imaging apparatus.

BACKGROUND ART

Medical imaging apparatuses (modalities) represented by ultra sonographic apparatuses, X-ray diagnostic apparatuses, computed tomography (CT), magnetic resonance imaging (MRI) and the like are widely adopted as apparatuses for performing measurements on various sites in the body of a human subject. Among such medical imaging apparatuses, an ultrasonographic apparatus, for example, is designed to transmit ultrasonic waves inside a test subject using an ultrasonic probe and receive ultrasonic reflection waves (echoes) resulting from differences in acoustic impedances between test subject tissues. On the basis of electric signals obtained through this reception, ultrasound tomographic images representing the structure of the internal tissue of the test subject is generated and displayed on a monitor or the like. The ultrasonographic apparatus is little invasive to the test subject and enables real-time observation of the state of in-body tissue by means of tomographic images and the like, and is therefore widely used for morphological diagnosis of a human body.

This type of ultrasonic element is also used for breast cancer diagnosis, for example. Currently, however, use of an ultrasonic apparatus alone for breast cancer examinations aiming at early detection of breast cancer is not recommended in Japan. One of the reasons therefor is that, in diagnoses by clinical laboratory technologist or the like, operating a conventional handheld ultrasonic scanner, it is extremely difficult to thoroughly examine the entire region of the breast and such diagnoses incur costs and time. It is also known that breast imaging and interpretation of breast images, in particular, require experience and know-how of an operator (physician, technologist, etc.) and diagnosis results are largely dependent on the skill of the operator.

Against this background, automated scanning-type apparatuses for imaging the entire breast, which allow for the entire breast to be scanned without being dependent on the skill of an operator, have been proposed. For example, Patent Document 1 discloses a method in which a water tank is provided in a measurement table, an ultrasonic probe is provided on the bottom surface of the water tank, and the breast being hung in the water tank is scanned along a cross-section vertical to the bottom surface to acquire a sagittal image. Patent Document 2 discloses a method in which an ultrasonic element is moved to perform scanning in the direction perpendicular to the bottom surface of a water tank to capture coronal images.

PRIOR ART DOCUMENT

Patent Documents

Patent Document 1: WO2003/101303
Patent Document 2: JP 2013-519455 A

SUMMARY OF THE INVENTION

Problem to be Solved by Invention

In such automated scanning-type test subject imaging, it is important to accurately detect an initial location where to begin the imaging (or a termination location where to terminate the imaging) from the standpoint of thoroughly examining the entire in-body tissue of the test subject as a test target and maintaining measurement precision. In this regard, one conceivable method for determining the initial location for imaging is a method in which the location is determined on the basis of information that is obtained from the body surface tissue of the test subject by means of a well-known conventional camera, laser scanner, or the like. However, although this information based on the body surface tissue of the test subject can be used to measure the location of the test subject within the imaged region, it is not easy to accurately estimate from such information the location of the mammary gland or other such in-body tissue in the test subject as a measurement target. The forms of the test subjects, in particular, show significant individual differences, and the locations and proportions of internal tissues may not necessarily be uniform. Furthermore, deformation of the test subject between before and after a surgery such as partial extirpation is inevitable, and features of the surface of the test subject serving as a reference are also affected. In cases like this, if features of the surface of the test subject are used as a reference for the location, it may be difficult to ensure that the entirety of the in-body tissue to be imaged will be encompassed in the imaged region.

Moreover, with such automated scanning-type test subject imaging, there are cases where a portion of the region of the measurement target fails to undergo measurement due to reasons such as deviation in the positional relationship between a measurement device and the test subject during measurement. For example, when slices are to be captured while moving the image plane and even if a method based on continuous acquisition of B-mode images of sagittal cross-sectional images, called an automated breast ultrasound system (ABUS) or automated breast volume scanning (ABVS), is used, there is the same problem, namely that it is necessary to confirm slice omissions. In such techniques, however, the orientations of the cross-sections may not necessarily be parallel, so when there is an omission, the omission cannot be ascertained as a simple lack of a slice. Moreover, when the probe is moved while being in contact with the subject, deformation of the subject inevitably occurs as a result, so, in this case as well, it is also difficult to determine that the omission is a simple lack of a slice.

In view of these problems, an object of the present invention is to acquire data which exhaustively represents the entirety of a measurement target site in a medical imaging apparatus.

Solution to Problem

An embodiment of the present invention is a medical imaging apparatus, as shown in FIGS. 1B to 3 and FIG. 7A, for example, a bath tank for accommodating a test subject, the test subject being at least a portion of a body of a human subject; a measurement device movable in a predetermined direction, the measurement device including ab group of elements to emit a radiation wave into the bath tank and receive a scattered radiation wave; and a control unit for measuring by the measurement device when at least one of a location of the test subject within a plane orthogonal to the predetermined direction, a location of the test subject in the predetermined direction, and continuity of data measured by the measurement device satisfies a predetermined condition.

Preferably, the control unit determines the location of the test subject on the basis of a location of a predetermined in-body tissue of the human subject.

Preferably, the control unit determines an initial location where the measurement device starts measurement and/or a termination location where the measurement device terminates measurement, on the basis of the location of the predetermined in-body tissue of the human subject.

Preferably, the predetermined in-body tissue is an in-body tissue located on the opposite side from a region subject to measurement by the measurement device relative to the initial location where the measurement device starts measurement or the termination location where the measurement device terminates measurement.

Preferably, the test subject is a breast of the human subject and the in-body tissue is a rib, chest wall, or pectoralis major muscle of the human subject.

Preferably, the medical imaging apparatus further comprising a location detection unit for detecting the location of the test subject within the plane orthogonal to the predetermined direction and/or the location of the test subject in the predetermined direction, the location detection unit comprising a location detection ultrasonic element.

Preferably, the location detection unit comprises: a first location detection unit for detecting the location of the test subject within the plane orthogonal to the predetermined direction; and a second location detection unit for detecting the location of the test subject in the predetermined direction, and at least one of the first location detection unit and the second location detection unit is comprised of the location detection ultrasonic element.

Preferably, the radiation wave is an ultrasonic wave and the group of elements is a group of ultrasonic elements for measurement.

Preferably, the radiation wave is an ultrasonic wave, the group of elements is a group of ultrasonic elements for measurement, and the location detection ultrasonic element is constituted by a plurality of groups of the ultrasonic elements for measurement being used to also serve as the location detection ultrasonic element.

Preferably, the medical imaging apparatus further comprising: a report unit for issuing a report if the control unit determines that the location of the test subject is not within a predetermined range.

Preferably, the report unit provides guidance for a movement destination of the test subject.

Preferably, if the measured location of the test subject is within the predetermined range, the control unit starts a processing for measuring data continuously while moving the measurement device in the predetermined direction.

Preferably, if it is determined that degree of deviation in the location of the test subject or discontinuity of the data measured at time of measurement does not satisfy the predetermined condition, the control unit performs any of: a processing in which the measurement is continued and the measured data is corrected; a processing in which the location of the measurement device in a movement direction is returned by a predetermined distance and the measurement is redone; and a processing in which the measurement is restarted from beginning.

Preferably, the process in which the measurement is continued and the measured data is corrected is performed if it is determined that the degree of deviation in the location of the test subject or the discontinuity of the measured data exceeds a first acceptable range serving as the predetermined condition, the process in which the location of the measurement device in the movement direction is returned by the predetermined distance and measurement is redone is performed if it is determined that the degree of deviation in the location of the test subject or the discontinuity of the measured data exceeds a second acceptable range serving as the predetermined condition, and the process in which measurement is restarted from the beginning is performed if it is determined that the degree of deviation in the location of the test subject or the discontinuity of the measured data exceeds a third acceptable range serving as the predetermined condition, the first acceptable range, the second acceptable range, and the third acceptable range being mutually different numerical ranges.

Preferably, the determination on whether the degree of deviation in the location of the test subject or the discontinuity of the measured data satisfies the predetermined condition is made on the basis of a predetermined algorithm.

Preferably, the predetermined algorithm is configured to compare an amount of shift in a cross-sectional area or a location of a center of gravity of the test subject with an amount of shift serving as the predetermined condition.

Preferably, the predetermined algorithm is configured to determine a value of correlation between image patterns of consecutive pieces of the measured data using an image correlation method, and to compare the value of correlation with a value of correlation serving as the predetermined condition.

Preferably, the predetermined algorithm is configured to compare an amount of shift in a geometric shape of a segment identified in the measured data with an amount of shift serving as the predetermined condition.

Another embodiment of the present invention is a program for a medical imaging apparatus to execute steps, the medical imaging apparatus, for example, a bath tank for accommodating a test subject, the test subject being at least a portion of a body of a human subject; and a measurement device movable in a predetermined direction, the measurement device including a group of elements to emit a radiation wave into the bath tank and receive scattered radiation wave; the steps comprising: a step of determining whether at least one of a location of the test subject within a plane orthogonal to the predetermined direction, a location of the test subject in the predetermined direction, and continuity of data measured by the measurement device satisfies a predetermined condition, and a step of using a result of the determination to determine whether to perform measurement with the measurement device.

Effect of Invention

According to the present invention, data exhaustively representing the entirety of a measurement target site can be acquired in a medical imaging apparatus.

BRIEF DESCRIPTION OF DRAWINGS

FIG. 4A to FIG. 4D are diagrams, schematically illustrating positional relationships between a breast structure and a ring array 220.

FIG. 8C(a) and FIG. 8C(b) are diagrams, illustrating a change in the cross-sectional area of the breast and a change in the location of the center of gravity of the breast in a condition in which the breast is moving in the depth direction.

DESCRIPTION OF EMBODIMENTS

This application is based on the Patent Application No. 2017-192802 filed on Oct. 2, 2017 in Japan, the contents of which are hereby incorporated in its entirety by reference into the present application, as part thereof.

The present invention will become more fully understood from the detailed description given hereinbelow. Further range of application of the present invention will become clearer from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

Figure 1A:
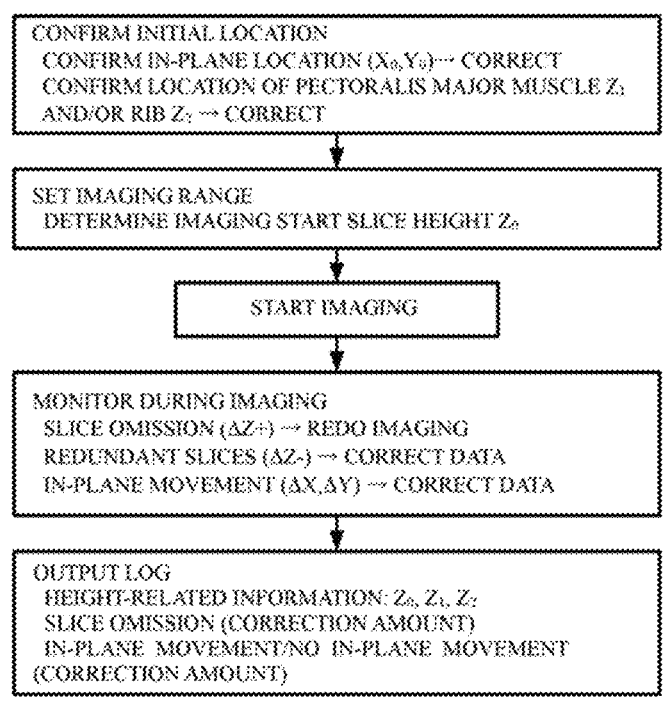
FIG. 1A is a conceptual diagram, comprehensively illustrating principal functions and flow of the present invention.

FIG. 1A is a conceptual diagram, comprehensively illustrating principal functions and flow of the present invention. Although imaging is performed by setting an imaging range as in known methods, the present invention is characterized in that: anatomical feature locations Z1 and Z2 are measured during confirmation of initial locations of a group of elements of a measurement device, and an imaging range (Z0) is determined on the basis of same; a location (X0, Y0) is confirmed within an image plane of a subject and a correction request is output according to need; an movement in the Z direction ($\Delta Z$) and an in-plane movement ($\Delta X$, $\Delta Y$) are monitored during imaging and an imaging sequence is corrected according to need; and in relation to imaging results, logs relating to the validity of the imaging range and the validity of volume data are output along with image data.

Figure 1B:
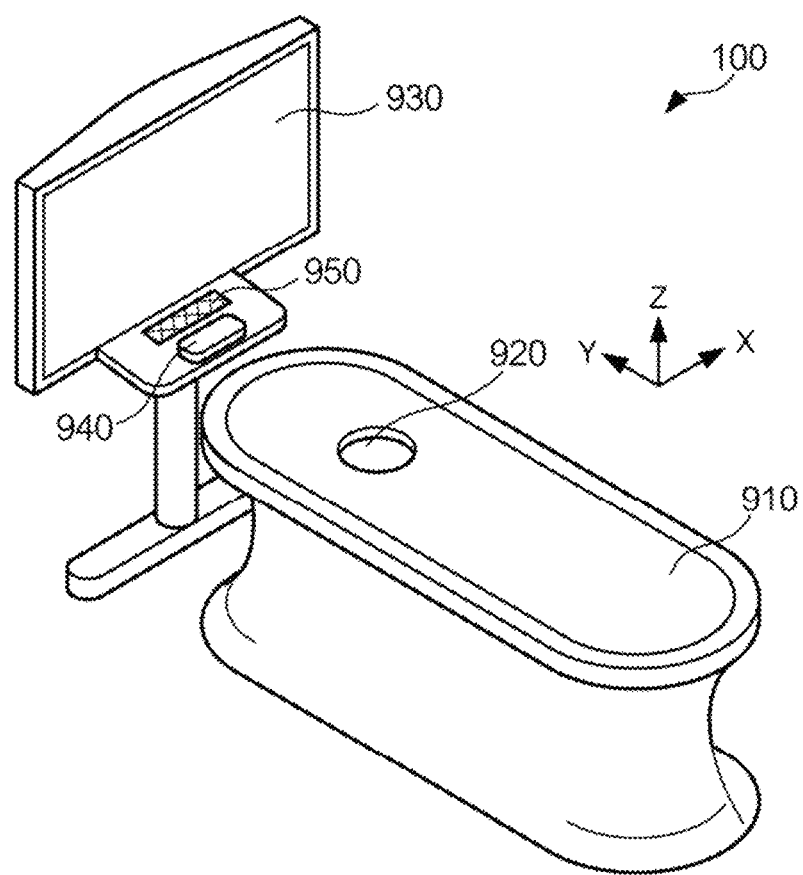
FIG. 1B is a diagram, illustrating an external appearance of an ultrasonographic apparatus 100.

The embodiment presented below will give a specific description of a case where an ultrasonographic apparatus 100 is used as a medical imaging apparatus and a breast is used as a test subject. FIG. 1B illustrates the external appearance of the ultrasonographic apparatus 100 serving as an embodiment of the present invention. The ultrasonographic apparatus 100 (also referred to as "ultrasound computer tomography (CT)") includes a measurement table 910, a reading device 940, a microphone/speaker 950, and a touch panel 930. The measurement table 910 serves to allow a human subject to be laid thereon horizontally (the X-Y plane in FIG. 1B) with the face down. The measurement table 910 may be inclined with respect to the horizontal plane and the surface thereof may not be flat. The reading device 940 is used to read barcodes or two-dimensional codes constituted by a printed-form of information or used to read information stored in a recording medium such as an integrated circuit (IC) card in which a memory chip is embedded. Information to be read may include, for example, information for identifying each human subject (IDs) as well as information pertaining to the human subject (age, gender, anamnesis, test history, test items, etc., which hereafter will be collectively referred to as "user information"). The user information may be pre-registered by the human subject or an operator.

An opening section 920 through which the test subject (breast) is to be inserted is formed in the front part of the measurement table 910. A measurement module 200 (see FIG. 2) for performing measurements on the test subject is provided in the opening section 920. Note that the position, size, and shape of the opening section 920 are merely exemplified. Moreover, there may be provided two such opening sections 920 at positions corresponding to the left and right breasts.

The touch panel 930 is a liquid crystal touch panel screen, which displays images or letters/characters and through which the human subject can input information in the ultrasonographic apparatus 100. The microphone/speaker 950 is constituted by a microphone and a speaker and is used by the human subject when inputting information by means of screen operation or voice or is used to report to the human subject information representing the state of a test or other relevant information for appropriately performing measurements.

A physician, medical personnel, or other operator who performs, supervises, or assists in a diagnosis made using the ultrasonographic apparatus 100 may be present in the vicinity of the ultrasonographic apparatus 100 in addition to the human subject. In this case, the person to whom the information is to be reported may not be the human subject but the operator, or may be both the human subject and the operator. Accordingly, the position or orientation of the setting of the touch panel 930 or the microphone/speaker 950 may be varied, as appropriate, according to the person to whom the information is to be reported. The touch panel 930 and the microphone/speaker 950 may be formed as devices that are independent of the measurement table 910 or may be formed integrally with the measurement table 910. The touch panel 930 may be provided at an arbitrary position and may, for example, be embedded in the measurement table 910 further on the front side than the opening section 920 so that the human subject with the face down can look into the touch panel 930.

Figure 2:
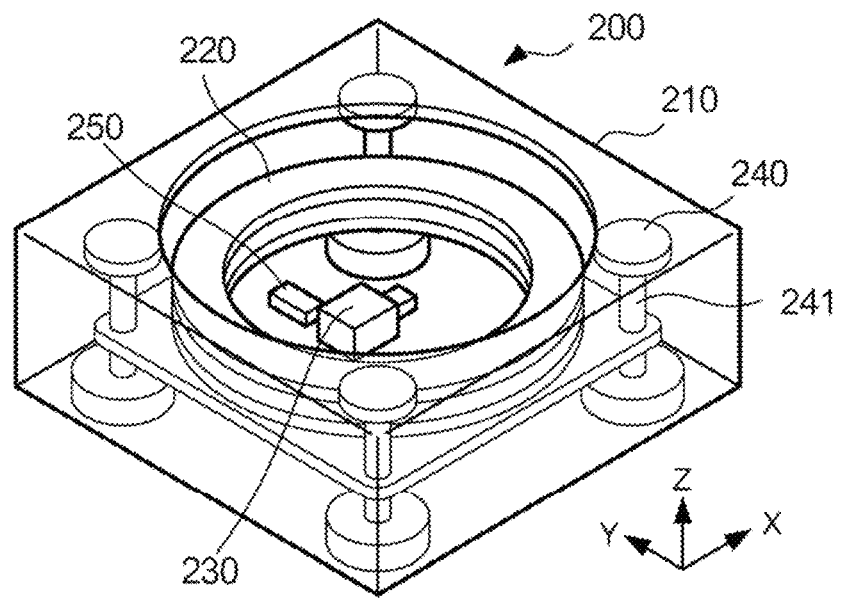
FIG. 2 is a diagram, illustrating an outline of a structure of a measurement module 200.

FIG. 2 illustrates the outline of an example of the structure of the measurement module 200. The measurement module 200 includes a bath tank 210 and a ring array 220. The bath tank 210 is a container in which deaerated water or other such medium having favorable ultrasound propagation properties is introduced and held during measurement. The bath tank 210 accommodates at least a portion of one breast of the human subject. The measurement module 200 is provided with a mechanism including valves and tubes for connection (not shown). The mechanism is used to introduce and discharge water into/from the bath tank 210.

The ring array 220 is a measurement device for performing measurement on the test subject and is an ultrasonic element group including a plurality of ultrasonic elements disposed in a planar form (in the X-Y plane in this example) for measurement and serving to emit ultrasonic waves into the bath tank and to receive ultrasonic waves as the scattered radiation waves. The ring array 220 converts an electric signal into an ultrasonic wave, uses a plurality of oscillators to generate an ultrasonic beam while adjusting the phases or the like of the oscillators and emit the ultrasonic beam toward a measurement target, receives a plurality of scattered ultrasonic waves from the test subject, and converts each of the scattered ultrasonic waves into electric signals and outputs same. Accordingly, information on a cross-section of tissue inside the test subject located in the plane in which the ultrasonic element group is disposed (X-Y plane) is obtained. The scattered ultrasonic waves include reflected waves and/or transmitted waves. That is to say, the ring array 220 may be of a type which receives reflected waves, a type which receives transmitted waves, or a type which receives both reflected waves and transmitted waves.

The shape of the ring array 220 may be circular, elliptical, or polygonal. The ring array 220 may be a single piece or be formed by arraying one or more elements constituting a unit in a prescribed shape, such as a ring shape, for example. The planar shape of the ring array 220 may be other than a ring shape, and may be a semi-circular shape or a C-shape. Alternatively, there may be employed a linear array in which elements are disposed in a linear shape.

A support member 240 is used to fix the ring array 220 on the bath tank 210 so as to be movable in a predetermined direction. The support member 240 includes a moving mechanism 241. Ultrasonic measurement is carried out while the ring array 220 is moved in order to repeatedly acquire information each representing a captured cross-section of a different location; thus, information on the tissue of the entirety of the breast interior can be acquired. In the example in FIG. 2, the moving mechanism 241 is represented in the form of a slide mechanism for moving the ring array 220 in the depth direction (Z direction). A scanning interval of 1 mm may be adopted, for example; accordingly, if the depth of the measurement range is 20 mm, a total of 21 tomographic images can be obtained. Note that although the scanning direction may be from top to bottom or from bottom to top, it is preferred to scan unidirectionally. The ring array 220 that is used to scan in a top-to-bottom direction will be described in the following embodiment.

The scanning direction need not be perpendicular to the image plane. The moving mechanism 241 may, for example, be designed so as to be capable of a movement that combines rotating motion and parallel movement, as represented by spiral motion. Essentially, it is sufficient if ultrasonic waves can be emitted in such a way that the entire range of the test target in the breast being hung into a water tank would be covered. As such, if the emitted beam can be controlled, then "movement" of the ring array 220 may involve the movement of only the measurement location due to control of the ultrasonic beam emission direction, and does not necessarily have to involve physical movement of the ring array 220 by use of the moving mechanism 241 or the like.

The measurement module 200 further includes a means for identifying the location of the test subject as one of the principal functions of the present invention. This means for identifying the location of the test subject demonstrates the advantageous effect described later in terms of identifying the location of the test subject on the basis of the location of in-body tissue, not the location of body surface tissue. As a specific configuration relating to this means, the measurement module 200 includes a location detection unit 130 (see FIG. 7A) for detecting the location of the test subject. The location detection unit includes a first location detection unit 131 (see FIG. 7A) for detecting the location of the test subject within the plane (X-Y plane) and a second location detection unit 132 (see FIG. 7A) for detecting the location of the test subject in the depth direction (Z direction). Either one or both of the two location detection units are formed from the means for identifying the location of the test subject on the basis of the location of the in-body tissue.

The means for identifying the location of the test subject on the basis of the location of the in-body tissue is a location detection ultrasonic element, for example. A specific method for detecting the location of the test subject using the location detection ultrasonic element will be described later. will be described in the following embodiment In the following embodiment, as shown in FIG. 2, a location detection ultrasonic element 230 (hereinafter referred to simply as "ultrasonic element 230") is used as the second location detection unit and a camera 250 is used as the first location detection unit.

The ultrasonic element 230 carries out ultrasonic measurement on the breast inserted in the bath tank 210 to detect the location of the breast, more specifically, detect whether the entirety of the breast has been inserted in the bath tank 210. For example, the location of an in-body tissue other than the breast, such as the pectoralis major muscle, chest wall, or ribs located on the upper side of the opening section when the breast is inserted through the opening section, can be detected or measured independently of the form (specifically, size and shape) of the breast.)

Generally speaking, ultrasound reflection intensity at a boundary between two types of substances having dissimilar compositions is determined by the acoustic impedance $z1$ of the substance in front of the boundary and the acoustic impedance z2 of the substance behind the boundary, and is expressed by the relationship 'reflection intensity=$|z1-z2|/(z1+z2)$'. The acoustic impedances of water, skin, fat, mammary gland, and bone are about 1.5, 1.76, 1.44, 1.60, and 6-7, respectively, and reflection at the boundary between a bone and another substance is found to be significantly higher than that of the others (there are individual differences for all of these substances, but for a bone, in particular, since the acoustic impedance differs significantly between the cortical bone portion and the cancellous bone portion, individual differences and differences between both portions are significant). Accordingly, a bone can be recognized easiest when extracting an in-body substance during image recognition. For ultrasonic echo images, in general, in order to display information over a wide brightness range, Log compression is carried out for the brightness and the brightness is displayed in terms dB. When extracting substances with a significant brightness difference, such as a bone, however, it is desirable to select image information that has not yet undergone Log compression or a parameter according to which the degree of compression is low.

Breast cancer is generally known to occur from within a breast duct. So, when scanning is performed by moving a ring-shaped device up and down with the intention to achieve imaging without omissions, if the imaging of an ultrasonic image encompasses a range extending up to the boundary between the mammary gland and pectoralis major muscle, at least a portion of the breast cancer will be included in the imaging field even if it is difficult to capture the entire volume of the breast cancer. The simplest, hence desirable, method for estimating the location of the boundary plane between the mammary gland and pectoralis major muscle would be to identify the location and orientation of a plane along which ribs defining a plane that is substantially parallel to the boundary plane are aligned. For this purpose, it is preferred that the locations of a plurality of ribs be detected from the image and the orientation of the plane encompassing the plurality of ribs be estimated from the standpoint of determining the validity of the initial location (or the termination location) of the imaging of the ultrasonic image.

The ultrasonic element 230 has such characteristics that, as described above, high reflection (high brightness) is detected at the boundary portion between two types of substances having dissimilar compositions. Accordingly, for the method for detecting the initial location of imaging, it is possible to directly detect the boundary between the mammary gland and pectoralis major muscle from the detected brightness information, rather than using the locations of the ribs as mentioned above. With both these methods, the detection of the location of the test subject that is based on the in-body tissue of the test subject and uses the ultrasonic element 230 enables the detection of the test subject location directly from the detected brightness information, as compared to conventional detection of the location of the test subject that is based on the body surface tissue of the test subject and uses a camera or the like; thus, a more simple yet highly precise estimation of the test subject location can be achieved. In particular, when determining the initial location of the ring array 220 (or the termination location if the ring array 220 is designed to scan from bottom to top), since the aforementioned location of the in-body tissue (ribs and/or pectoralis major muscle) is used as a reference for the initial location, the initial location can be determined simply and highly precisely.

If the coordinates of the image captured using the ring array are defined as X and Y coordinates, the ultrasonic element 230 can also acquire the Z coordinate in relation to the X and Y coordinates. Accordingly, the acquired information can be used as a parameter to assist correction when reconstructing a plurality of images resulting from capturing 3D volume images of the breast have been captured, or used for left and right comparison or change-over-time comparison. Compensation for a slice omission is also made possible.

It is preferred that an ultrasonic element array be used for the ultrasonic element 230. The ultrasonic element 230 installation location may be the bottom surface of the bath tank 210 or a side surface of the bath tank 210, or the ultrasonic element 230 may be fixed to the ring array 220 and may also be provided in a plurality. Wherever the installation location might be, since the interior of the bath tank 210 is filled with a medium constituted by deaerated water or the like, there is no need to bring the ultrasonic element 230 into contact with the test subject and the installation work is easy. Further, the measurement module 200 of this embodiment includes the ultrasonic element 230 as a separate member from the ring array 220, but the ultrasonic element forming the ring array 220 may also be used to serve as the ultrasonic element 230. In this case, if the ultrasonic element of the ring array 220 that is used to serve as the ultrasonic element 230 is configured to be capable of swinging in the Z direction, for example, then measurement results equivalent to the aforementioned measurement results obtained with the ultrasonic element 230 can be obtained and, moreover, a difference between sound velocities of tissues within the plane obtained by the ring array 220 can be used to measure the location of the tissue in the depth direction. Meanwhile, if it is sufficient to only provide the function of measuring the distance to the breast surface or the function of determining a coordinate on the Z axis, then a laser scanner or other such devices that carry out optical distance measurement, visible light image sensors, sensors using X-rays, or other such location detection sensors may be used as a substitute for the ultrasonic element 230. In this case, it is preferable to use a location detection ultrasonic element in place of the camera 250 serving as the first location detection unit from the standpoint of achieving a simple yet highly precise estimation of the test subject location through the detection of the test subject location based on the in-body tissue of the test subject.

The camera 250 may be a camera including, for example, an imaging element and a mechanism for controlling focus adjustment and the like, and may optically image the breast in the bath tank 210 to acquire information relating to the location of the breast or changes in the location of the breast. The camera 250 may be fixed to the bottom of the bath tank 210 on the inside the bath tank 210 so as to be submerged, or may be provided on the outer side of the bottom or a side surface of the bath tank 210. Note that instead of a camera, there may be used a location detection ultrasonic element, a location detection sensor using laser light, etc., or other such means capable of acquiring information relating to the location of the breast or changes in the location of the breast to acquire information relating the location of the breast or changes in the location of the breast. When a location detection ultrasonic element is used instead of a camera, the installation location thereof may be the bottom surface of the water tank or a side surface of the bath tank 210, or the location detection ultrasonic element may be fixed to the ring array 220, similarly to the ultrasonic element 230. Moreover, the ultrasonic element forming the ring array 220 may be used also to serve as this location detection ultrasonic element for detecting the location of the breast within the plane.

The measurement module 200 above uses separate detection means to carry out determination for detecting the location of the test subject in the X-Y plane and for detecting the location of the test subject in the Z direction, but the present invention is not limited to such a configuration. For example, a variety of modifications may be adopted, such as a configuration in which a single detection means is used to detect three-dimensional locations, i.e. locations in the X-Y plane and the Z direction, or a configuration in which the detection of the test subject location using a detection means is only carried out in the Z direction.

Figure 3:
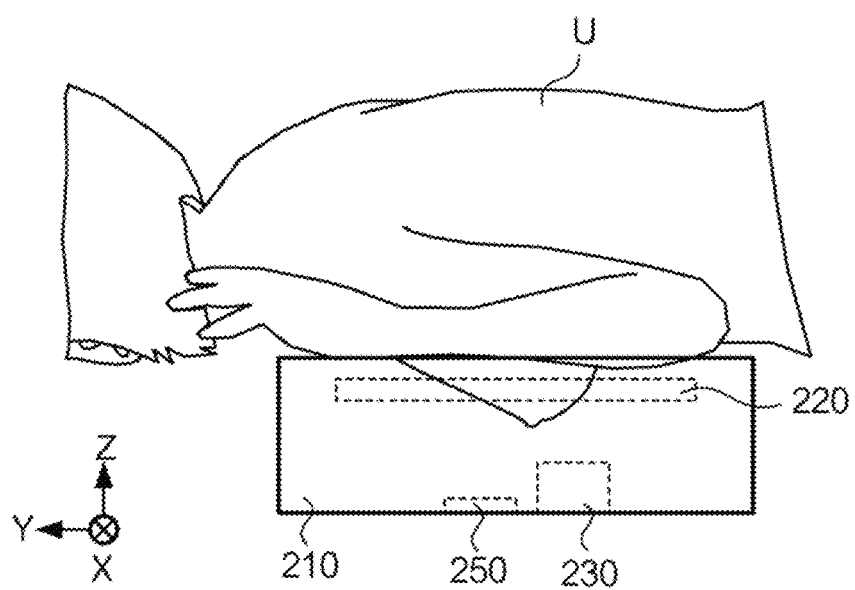
FIG. 3 is a diagram, illustrating a state in which measurement by the ultrasonographic apparatus 100 is carried out.
Figure 5A:
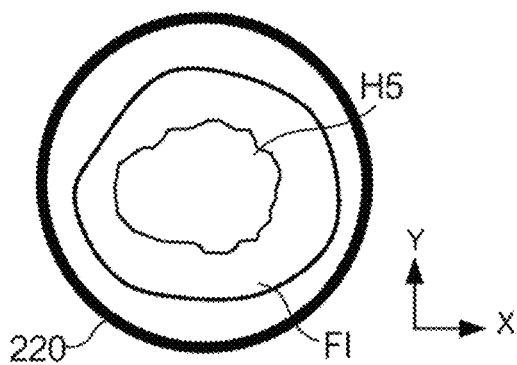
FIG. 5A to FIG. 5D are diagrams, schematically illustrating images obtained according to different locations of the ring array 220.
Figure 5B:
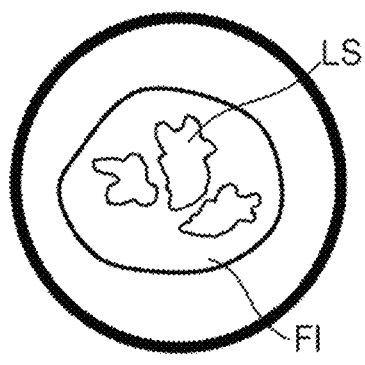
Figure 5C:
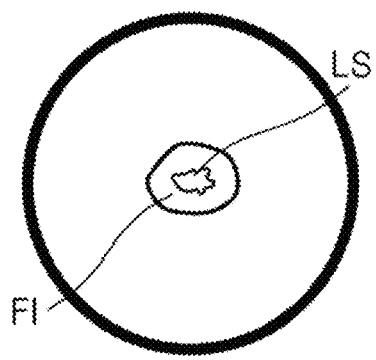
Figure 5D:
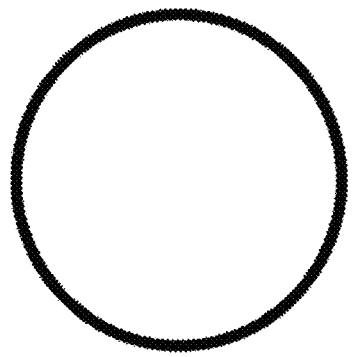

FIG. 3 illustrates a state in which measurement by the ultrasonographic apparatus 100 is carried out. The measurement is carried out in a state in which a human subject U is lying with the face down (in a prone position) such that at least a portion of one breast of the human subject U is inserted through the opening section 920. In other words, in a state in which the breast is being hung in the bath tank 210, the ultrasonographic apparatus 100 causes the ring array 220 to perform scanning so as to collect data on the entire region of the test target in the breast as the test subject. The measurement is carried out for each breast. In a case where only one opening section 920 is provided and the measurement is to be carried out on both breasts, the body posture is adjusted after completion of the measurement for one breast and then the other breast is inserted in the bath tank 210.

FIG. 4 and FIG. 5 schematically illustrate the positional relationship between the breast structure and the ring array 220. FIG. 4 illustrates cases where the ring array 220 is located at: FIG. 4A an upper limit location in the Z direction; FIG. 4C near the tip end of the breast (a location corresponding to the nipple); FIG. 4D a lower limit location in the Z direction; and FIG. 4B an intermediate location between the locations illustrated in FIG. 4A and FIG. 4C. LS denotes the mammary gland, FI denotes fatty tissue, H6 denotes skin, CO denotes a rib, H1 denotes a lactiferous sinus, H3 denotes a mammary gland lobe, H4 denotes a Cooper's ligament, H5 denotes the pectoralis major muscle, and H2 denotes a group of breast ducts.

FIG. 5 schematically illustrates images that are generated on the basis of ultrasonic measurement data obtained at the Z-direction locations illustrated in FIG. 4A, FIG. 4B, FIG. 4C, and FIG. 4D. For the sake of convenience, only the mammary gland LS and the fatty tissue FI are illustrated. By use of the sound velocity resolution of sound velocity distribution measurement in ultrasonic CT, the mammary gland or a muscle can be distinguished from fat in terms of sound velocity. Thus, although it is difficult to discern the boundary between the mammary gland and a muscle directly from a sound velocity image, ascertainment of a significant diminution in the proportion of the region of fat in the image plane, as illustrated in FIG. 4, makes it possible to confirm that the ring array is located at the boundary plane between the region of the mammary gland and the pectoralis major muscle. A method such as the following, for example, may be used for a specific sound velocity distribution measurement. That is, sound velocity distribution may be determined through a process of involving the acquisition of transmitted wave data and detecting the first value in a waveform from the acquired data, and solving an inverse problem for propagation time distribution data mapped onto a two-dimensional space of a transmission channel and a reception channel. There are numerous available examples of inverse problem solving techniques and, for example, an algebraic reconstruction technique may be adopted in which, for example: propagation time distribution data is calculated from an assumed sound velocity distribution; the assumed sound velocity distribution is corrected in such a way that the difference between the actually measured propagation time distribution and the propagation time distribution derived from the assumption decreases; and such a process is repeated until the value of the difference is sufficiently small. In this case, from the standpoint of enhancing precision, it is useful to estimate a refraction path on the basis of the Fermat's principle in the sound propagation time calculation, so this principle may be used.

Figure 6A:
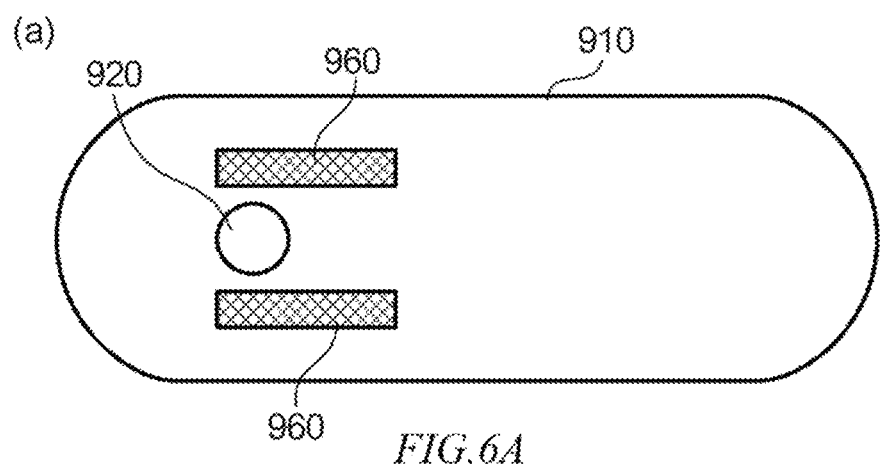
FIG. 6A and FIG. 6B are diagrams, illustrating examples of how a pressure sensor 960 may be disposed.
Figure 6B:
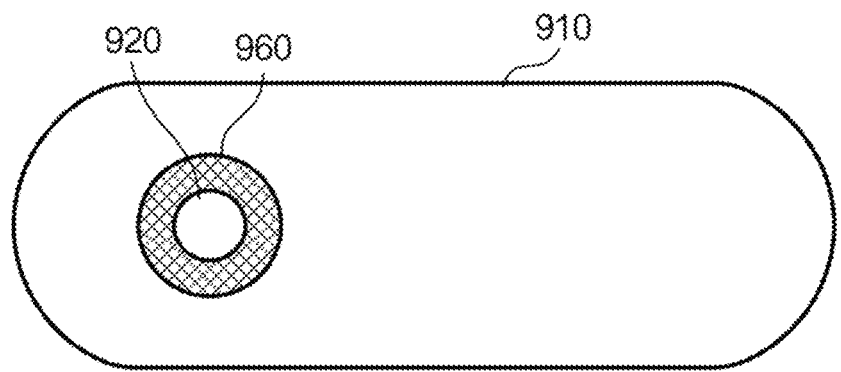

In FIG. 6A and FIG. 6B schematically illustrate the internal structure of the measurement table 910. A pressure sensor 960 is embedded inside the measurement table 910. The pressure sensor 960 is a piezoelectric element formed into a sheet shape and measures motions of the body of the human subject indirectly by measuring the load incurred by the human subject laid on the measurement table 910 and a change over time of the load. Note that the drawings only illustrate an example of the pressure sensor 960 and the location, number, and shape of the pressure sensor 960 are not limited to this example.

Figure 7A:
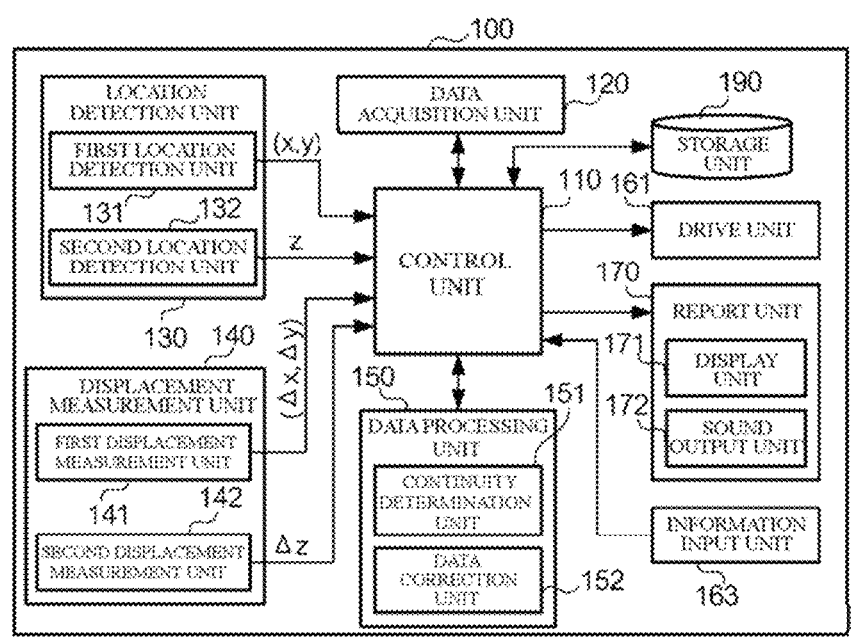
FIG. 7A is a functional block diagram of the ultrasonographic apparatus 100.

FIG. 7A illustrates the ultrasonographic apparatus 100 to which an example of a functional block diagram for performing the present invention has been applied. The ultrasonographic apparatus 100 includes a control unit 110, a data acquisition unit 120, a location detection unit 130, a displacement measurement unit 140, a data processing unit 150, a drive unit 161, an information input unit 163, a report unit 170, and a storage unit 190.

The storage unit 190 is a storage device such as a hard disc, semiconductor memory, etc., and stores a program for implementing the below-mentioned functions of the ultrasonographic apparatus 100, as well as information to be used by the control unit 110 or the data processing unit 150, such as the location of the breast or a change in the location of the breast and an algorithm and/or parameter used for determining the continuity of measured data. Moreover, correction data, a correction log, a log providing a basis for performing correction, a log for determining a range, etc. may also be stored, and preferably, these records are saved while being associated with a captured slice. The storage unit 190 may also store the user information described previously.

The location detection unit 130 includes the first location detection unit 131 and the second location detection unit 132, as described previously. The first location detection unit 131 may, for example, be implemented by the camera 250 and detect the location of the breast within the plane. The location within the plane may be defined, for example, using the location of the nipple of the breast or a location corresponding to the contour of the breast. The second location detection unit 132 may, for example, be implemented by the ultrasonic element 230 and detect the depth location of the breast.

The displacement measurement unit 140 includes a first displacement measurement unit 141 and a second displacement measurement unit 142. The first displacement measurement unit 141 may, for example, be implemented by the camera 250 and measure a change in the location of the breast within the plane (movement of the breast within the plane). The second displacement measurement unit 142 may, for example, be implemented by the ultrasonic element 230 and measure a change over time in the depth location of the breast (movement of the breast in the depth direction).

Note that an arbitrary device configuration may be adopted to implement the functions of the first location detection unit 131, the second location detection unit 132, the first displacement measurement unit 141, and the second displacement measurement unit 142. For example, all of the functions of the first location detection unit 131, the second location detection unit 132, the first displacement measurement unit 141, and the second displacement measurement unit 142 may be implemented by a single device (e.g. the ultrasonic element 230), or a single functional module included in the above four units may be implemented by two or more devices. In this case, for example, the function of the first displacement measurement unit 141 is implemented by a combination of the camera 250 and the pressure sensor 960, and the function of the second displacement measurement unit 142 is implemented by a combination of the ultrasonic element 230 and the pressure sensor 960. Alternatively, the ring array 220 may be used to determine the location and/or determine the displacement. In other words, the data acquisition unit 120 will also function as the location detection unit 130 and/or the displacement measurement unit 140. Further, if the ultrasonographic apparatus 100 includes sensors other than the above (a temperature sensor for measuring the temperature inside the bath tank 210, a sensor for detecting the presence of foreign matter inside the bath tank 210, etc.), these sensors may be utilized to implement the function(s) of the location detection unit 130 and/or the displacement measurement unit 140.

The data processing unit 150 may be implemented by a processor for processing images or the like, and under the control of the control unit 110, generates image data on the basis of measurement data from the ring array 220. The data processing unit 150 includes a continuity determination unit 151 and a data correction unit 152. The continuity determination unit 151 determines the continuity of data measured by the ring array 220. The data correction unit 152 determines whether data needs to be corrected on the basis of the degree of the continuity obtained by the continuity determination unit 151, and if it is determined that correction is needed, corrects the measurement data and/or the image data. The data before the correction and the data after the correction may be stored while being associated with each other. The "continuity" as referred to herein means that transition is made between adjacent values so as to demonstrate a certain degree of tendency, and the transition may involve local fluctuation resulting from an error or the like.

The drive unit 161 includes a motor and a mechanism for controlling the motor, and under the instruction of the control unit 110, controls the moving mechanism 241 so as to move the ring array 220 in the depth direction. The drive unit 161 reports the depth-direction location (scanning location) of the ring array 220 to the control unit 110 so as to enable the control unit 110 to determine the current location of the ring array and/or determine whether scanning of a pre-set range has been completed.

The information input unit 163 is implemented in the form of the reading device 940 and/or the touch panel 930 and is operated by the human subject or the operator, e.g. medical personnel, and used to input the user information and other such information required for measurement.

The report unit 170 includes a display unit 171 and a sound output unit 172 and issues a report by means of an audio, image, vibrations, etc. The display unit 171 may be implemented in the form of the touch panel 930 and the sound output unit 172 may be implemented in the form of the microphone/speaker 950, for example. The specific content of the report is such that the report unit 170 under the control of the control unit 110 reports information required in the course of measurement to the human subject and/or the medical personnel. The report may be issued, for example, when it is determined at the control unit 110 that the location of the breast is not within a predetermined range. In this case, the report unit 170 additionally provides information for providing guidance to the movement destination of the breast.

The data acquisition unit 120 may, for example, be implemented by the ring array 220 and operate under the control of the control unit 110.

The control unit 110 is implemented in the form of one or more processors and carries out measurement by the aforementioned ultrasonic element group in a case in which at least one from among (i) the location of the breast within a plane perpendicular to the predetermined direction, (ii) the location of the breast in the predetermined direction, and (iii) continuity of data measured by the ultrasonic element satisfies a predetermined condition.

Specifically, the control unit 110 first determines whether the initial location of the breast (a change in the location may also be used in addition) measured by the location detection unit 130 (the displacement measurement unit 140 may also be used in addition) is within a predetermined range, and if the result is affirmative, controls the data acquisition unit 120 and the drive unit 161 so as to start an ultrasonic measurement process for the breast interior while moving the ring array 220 to perform scanning. The in-plane location of the breast can be expressed using at least one from among the location of the nipple, the contour of the breast, and the center of gravity of the breast. The location of the breast in a direction (depth direction) perpendicular to the image plane can be identified with reference to the location of a predetermined in-body tissue (e.g. a rib) of the human subject other than the breast. The location of the breast to be identified may be a location (absolute location) that is determined in relation to the apparatus or a relative location that is determined with reference to the location of a predetermined in-body tissue. Further, for measurement for a mastectomized subject, the medical personnel may provide an identification mark to be used as a reference.

If the ultrasonic element of the ring array 220 is used to also serve as the second location detection unit 132, for example, the control unit 110 may carry out provisional measurement by moving the ring array 220 to perform scanning before performing the measurement, then discriminates between the sections of the captured internal tissues, such as the mammary gland, fat, muscle, etc. on the basis of the image data generated from the ultrasonic measurement data obtained at the data processing unit 150 to determine the plane corresponding to the boundary between fat and muscle, and thus determine whether the initial location of the breast in the depth direction is proper. Alternatively, in the provisional measurement, the data processing unit 150 may measure a change in the center of gravity of the breast and/or the cross-sectional area of the breast in the depth direction from the image data and determine the initial location of the breast in the depth direction on the basis of the continuity of the changes. If the breast is determined as being at an appropriate initial location in the provisional measurement, the process proceeds to the measurement.

The expression "within a predetermined range" may, for example, be defined by the amount by which the location of the breast deviates from a reference location and a change in the location. For example, with regard to the deviation in the in-plane location, the extent "within a predetermined range" may be defined as the central location of the nipple being within the region of a ±5 mm-radius circle from the reference location, whereas the deviation in the perpendicular direction is set to correspond to ±0.5 mm, and when it is confirmed that a state in which this condition is satisfied continues for 5 seconds or more, for example, it is determined that the location of the breast is within the predetermined range and the measurement can be continued. The extent "within a predetermined range" may be set for each measurement in accordance with the required precision, or a user may input a reference value in the apparatus at the time of measurement, for example, and it is preferred that the extent "within a predetermined range" be variable.

Next, the measurement is started at the initial location at which the ring array 220 starts the measurement. The initial location may be adjusted for each human subject. Now, the reason for which it is necessary to control the precision of the initial location in the horizontal plane will be described. That is, having the subject substantially at the same location in the horizontal plane makes it easier to compare volume data between the left and right and compare volume data for the observation of a change over time (comparison against past examination data, and/or determination of the effect of anti-cancer agents used in chemotherapy before surgery). In principle, as a matter of course, comparison is possible even when brightness volume data $I(x,y)$ turns to $I(x+\Delta x, y+\Delta y)$. In actuality, however, considering the presence of artifacts and image distortion, it is preferable that $\Delta x$ and $\Delta y$ be as small as possible. Here, a true value is $I_{true}(x,y)$, and the acquired image in relation to an artifact spatial distribution $I_{artifact}(x,y)$ is $I_{true}(x,y)+I_{artifact}(x,y)$. If the subject moves, the value becomes $I_{true}(x+\Delta x, y+\Delta y)+I_{artifact}(x,y)$, and if $I_{artifact}(x,y)$ is unknown, it will be difficult to compare the two with a correlation-based or other such methods (naturally, there are artifacts that move according to the movement of the subject and artifacts that are fixed with respect to the location of a ring; what is being discussed here is the effect of artifacts that are fixed to the location of the ring.) Moreover, image distortions occur in actual clinical images due to the influence of sound velocity unevenness, and the like. When distortion is expressed as a function $[X,Y]=f(x,y)$, since $[X+\Delta x, Y+\Delta y]=f(x+\Delta x, y+\Delta y)$ generally does not stand, it is preferred that the precision of the initial location be controlled such that situations in which $\Delta x$ and/or $\Delta y$ are large are avoided.

Figure 7B:
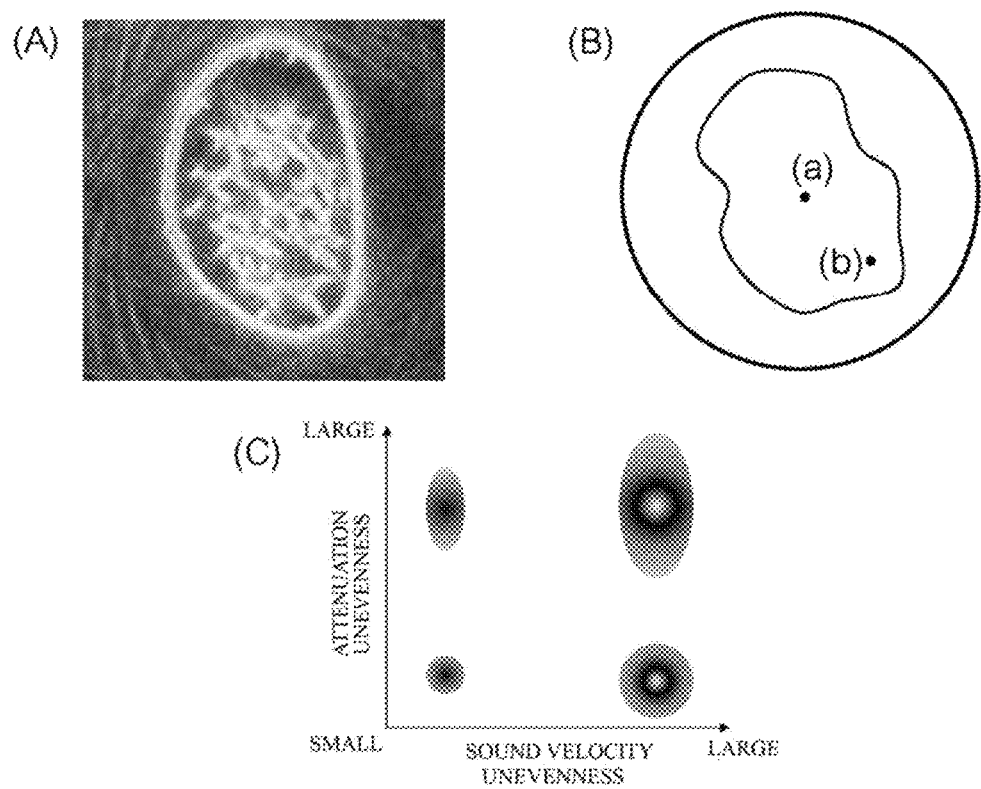
FIG. 7B is a diagram, illustrating an example of spatial distribution of artifacts.

An actual example of an artifact spatial distribution $I_{artifact}(x,y)$ is illustrated in (A) of FIG. 7B. The amount of artifacts is relatively large in the peripheral portion of the image than in the central portion, and the artifacts generally occur as a fixed pattern noise independently of the movement of the subject. Next, an example of image distortion will be described using (B) and (C) in FIG. 7B. As illustrated in (B), the way the image is distorted differs between a scatterer (a) of interest in the image central region and a scatterer (b) of interest in the image central region. The spatial resolution and the contrast resolution of an image can be evaluated using a point spread function. The point spread function is a function which indicates the way ideal point scatterers existing in the representation of a δ-function result in image formation in the form of a specific spatial brightness distribution, and in an ideal case, as illustrated in the lower left part of (C), the distribution assumes a two-dimensional Gaussian function distribution form. In other words, the distribution has a large value in the center and assumes a form that is isotropic in a two-dimensional plane, and the brightness decreases monotonously in conformity with distance from the center. In this regard, in imaging using the ring array, while, in the central portion, distances from the elements are isotropic and the distances of propagation within the body also are more or less uniform (because a cross-section of the breast can be often approximated by a circular shape). However, in a location such as the location of the scatterer (b), distances from the elements are uneven, and due to the effect of diffraction or energy dissipation, energy arriving at the location of the scatterer changes for each path, resulting in a possible distortion into an anisotropic form, as illustrated in the upper left part of (C). Moreover, the sound velocity being uneven results in unevenness in the arrival time estimation precision for each path, causing a distortion into a point spread function such as that illustrated in the lower right part of (C).

As indicated above, in this example, it is preferred that measurement by the ring array 220 be not started until it is confirmed that the breast is disposed at an appropriate location. In this way, it is possible to prevent omissions in the measurement on the tissue at the proximal end of the breast due to incomplete insertion of the breast. Moreover, as a result of guiding the breast to an appropriate location relative to the ring array in the horizontal plane, a decrease in the measurement precision due to differences in artifacts and/or differences in resolution corresponding to the location in the horizontal plane can be limited.

The control unit 110 also monitors the location of the breast during the measurement, and if it is determined that the predetermined condition is not satisfied, determines to perform at least one from among: a process in which although the measurement is continued, the measured data is corrected later; a process in which the ring array 220 is returned to a location corresponding to a time point prior to the current time point to redo the measurement; and a process in which the measurement is restarted from the beginning.

In a preferable mode, the control unit 110 sets levels to acceptability relating to the location of the breast and/or discontinuity of the data and carries out a different operation according to the level of deviation in the location having occurred or the data discontinuity. In order to carry out different operations, a different condition (acceptable range) for performing an operation may be set for each operation. For example, when it is determined that the degree of deviation in the location of the breast or the discontinuity of the data exceeds a first acceptable range, the process in which the measurement is continued and the measured data is corrected is preformed, whereas if it is determined that the same exceeds a second acceptable range that is milder than the first acceptable range, the process in which the scanning location of the ring array 220 is returned to a previous location and the measurement is redone is performed, and if it is determined that the same exceeds a third acceptable range that is milder than the second acceptable range, the process in which the measurement is restarted from the beginning is performed.

For the acceptable range relating to the location, the first acceptable range may be defined as the maximum value of the deviation within the plane detected per unit time being ±1 mm (millimeter) or less and the deviation in the depth direction being 0 mm or less, the second acceptable range may be defined as the deviation within the plane being ±2 mm or less and the deviation in the depth direction being 0.7 mm or less, and the third acceptable range may be defined as the maximum value of the deviation within the plane being ±3 mm or less and the deviation in the depth direction being ±1 mm or less, for example.

By setting stepwise levels of the acceptable range in this way, good reliability of the measured data and examination efficiency (time required for measurement) can both be achieved.

It is preferred that the degree of deviation in the location of the test subject or the discontinuity of the measured data be determined using a predetermined algorithm (condition). Examples of the predetermined algorithm include: an algorithm based on a comparison with the cross-sectional area or the amount of shift in the location of the center of gravity of the test subject; an algorithm based on the determination of a value of correlation between an image pattern of one measured data and an image pattern of another measured data; or an algorithm based on a comparison with the amount of shift in the geometric shape of a segment in measured data. Below, an example of the algorithm for determining the discontinuity of the measured data will be described using FIGS. 8A to 8G.

Figure 8A:
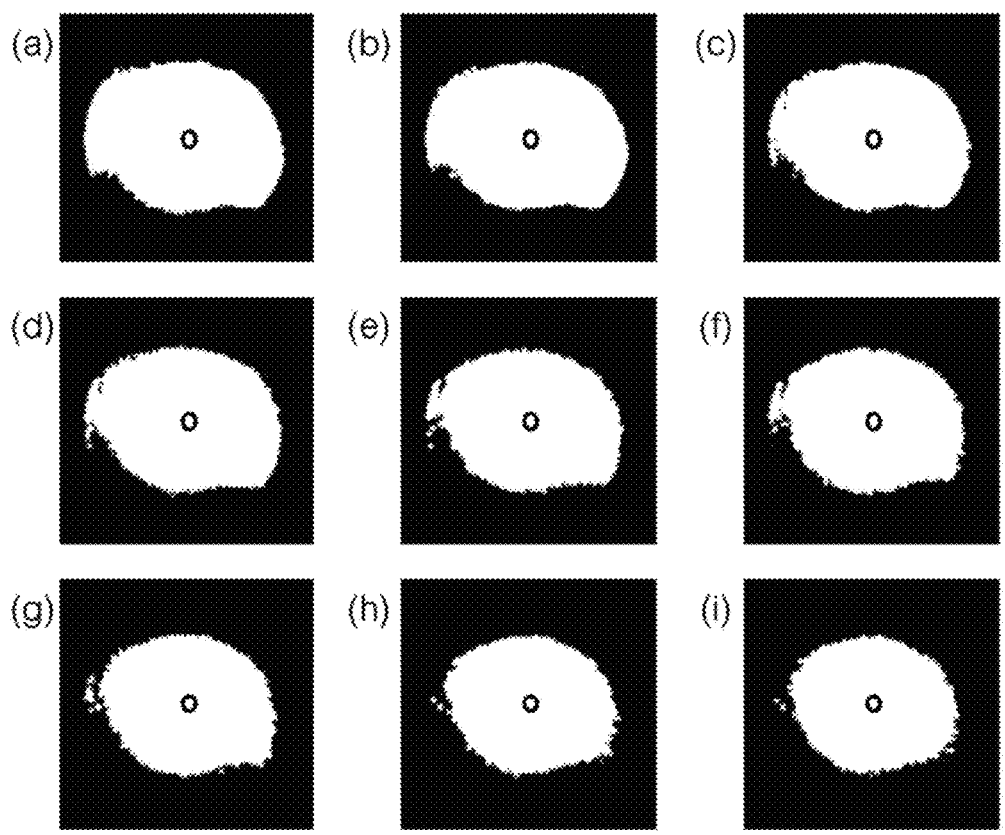
FIG. 8A is a diagram, illustrating an example of an image obtained by subjecting measured data to image processing.

FIG. 8A illustrates an example of images generated on the basis of the ultrasonic measurement data measured at various scanning locations. The images obtained from the ultrasonic measurement data obtained at the various scanning locations are further subjected to binarization processing to identify the contour of the breast, and the center of gravity of the breast is calculated from the contour and the location of the center of gravity is displayed. In this example, the images obtained at a total of 9 scanning locations from (a) to (i) are illustrated.

Hereafter, an image corresponding to each scanning location in the depth direction will be referred to as a "frame" and a serial number for uniquely identifying the location of the frame will be referred to as a "frame number". In other words, when scanning is performed from top to bottom in the depth direction (i.e. from the proximal end of the breast (on the side near the pectoralis major muscle) to the tip end of the breast (nipple side)), the frame number "1" indicates an image representing the cross-section of the breast closest to the proximal end thereof, and the last frame number indicates an image of the cross section of the breast closest to the tip end thereof.

Figure 8B:
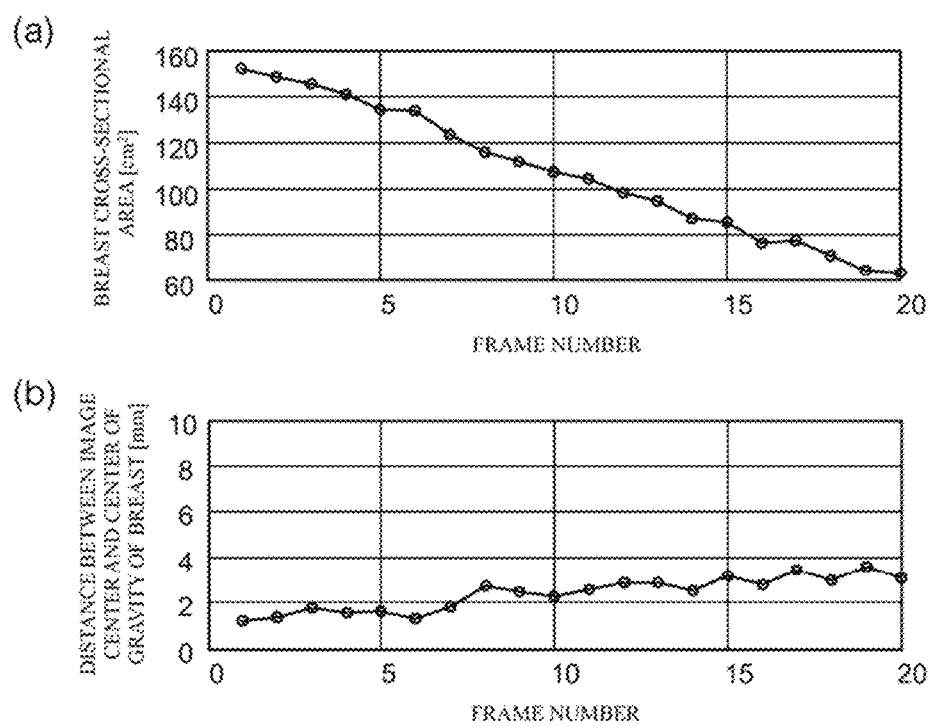
FIG. 8B(a) and FIG. 8B(b) are diagrams, illustrating a change in a cross-sectional area of the breast and a change in the location of the center of gravity of the breast in a condition in which the breast is not moving during measurement.

In FIG. 8B(a) and FIG. 8B(b) illustrate a change in the cross-sectional area of the breast and a change in the location of the center of gravity of the breast in a condition in which the breast is not moving during measurement (or moving only to a degree such that the breast can be regarded as essentially not moving during measurement). It can be seen that the cross-sectional area of the breast demonstrates a generally gentle decrease toward the tip end (as the frame number increases), reflecting the shape of the breast. Moreover, the distances from the image center to the center of gravity of the breast are more or less uniform. The reason therefor is that the location of the center of gravity of the breast usually does not significantly change between the tip end and the proximal end.

In FIG. 8C(a) and FIG. 8C(b) illustrate a change in the cross-sectional area of the breast and a change in the location of the center of gravity of the breast in a condition in which the breast is moving in the depth direction. When the breast moves in the depth direction, a discontinuous portion (gap) occurs in the data indicating the breast cross-sectional area. This example indicates that the breast moved in the depth direction during measurement between the ninth frame and the tenth frame. Meanwhile, no discontinuity is observed for the distance between the image center and the center of gravity of the breast, and this implies that the movement is made solely in the perpendicular direction.

Figure 8D:
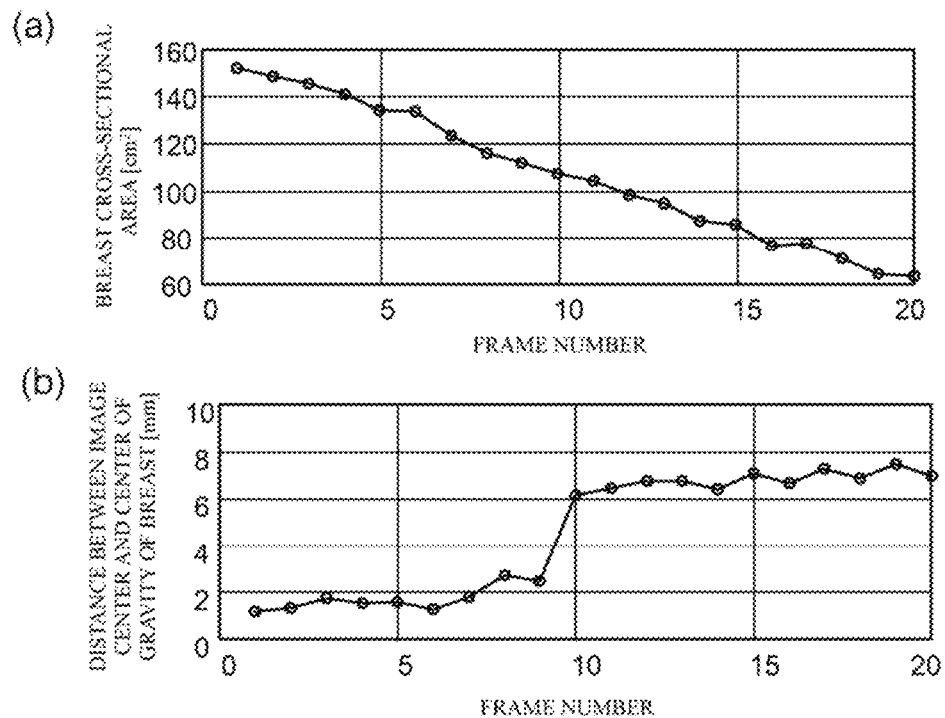
FIG. 8D(a) and FIG. 8D(b) are diagrams, illustrating a change in the cross-sectional area of the breast and a change in the location of the center of gravity of the breast in a condition in which the breast is moving in a horizontal plane.

In FIG. 8D(a) and FIG. 8D(b) illustrate a change in the cross-sectional area of the breast and a change in the location of the center of gravity of the breast in a condition in which the breast is moving in the horizontal plane. Although no gap is observed for the breast cross-sectional area, discontinuity can be seen for the distance between the image center and the center of gravity of the breast between the ninth frame and the tenth frame.

Figure 8E:
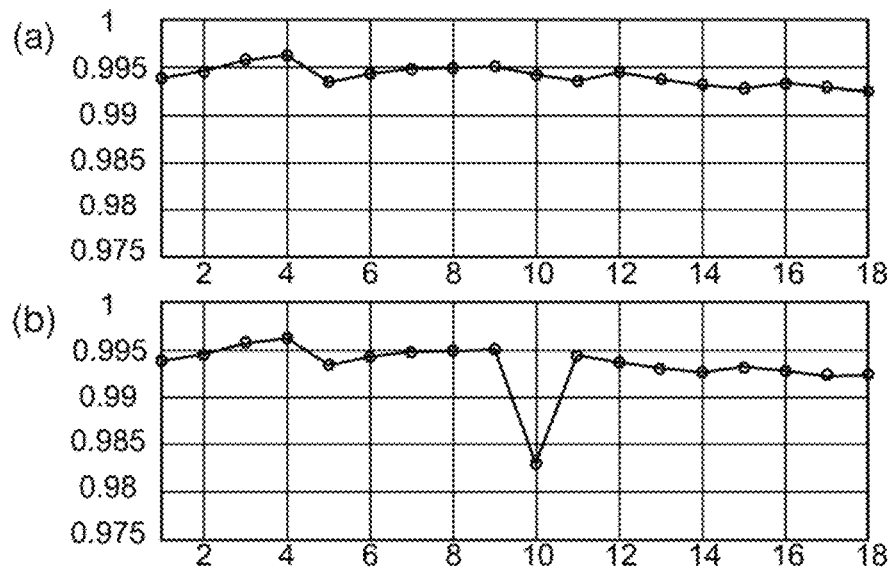
FIG. 8E(a) and FIG. 8E(b) are diagrams, illustrating changes in a cross-correlation between frame images in a condition in which the breast is moving.

In a different example, an image correlation technique may be adopted and structure size and/or the number of segments within the captured image may be monitored to carry out pattern matching, thereby determining whether the breast has moved and/or the degree of the movement. FIG. 8E illustrates a case where a correlation technique was applied to an actual image (B-mode image after Log compression). (a) represents a result when there was no movement during imaging and (b) represents a result when frame 10 was omitted due to an upward movement during imaging of frame 10 in an amount equivalent to a thickness corresponding to one frame. If the maximum value of the cross-correlation between frame i and frame j is expressed as $C_{i,j}$, the vertical axis in FIG. 8E indicates $C_{i,i+1}/\sqrt{C_{i,i}+C_{i+1,i+1}}$. It can be confirmed that the value of correlation drops significantly for frame 10 only in (b). A calculation having equivalent characteristics to the cross-correlation calculation, e.g. a squared error summation $S(m, n)=\Sigma\Sigma I((x, y)^2-I(x+m, y+n)_{i+1}^2/\Sigma\Sigma I(x, y)_i \times I(x, y)_{i+1})$, for example, may be used. The doubled $\Sigma$ represents summation in image spaces x and y, and m and n represent in-plane movement in unit pixel.

Such techniques (correlation calculation and equivalents of correlation calculation) are more sensitive to slice omissions than the tracking of changes in the cross-sectional area or the center of gravity. That is to say, while there might be an incidental match in the cross-sectional area or the center of gravity between different frames, with the cross-correlation calculation, it is highly improbable that all of the pixels of interest would show a match, so the value of cross-correlation being high is a highly precise implication of a probability that there is no frame omission. Further, the cross-correlation calculation also has an advantage in that in-plane movement (confirmed on the basis of a shift in the location corresponding to the maximum value) and movement in the depth direction are recognized separately; the tracking of changes in the cross-sectional area and/or the center of gravity does not allow for such separate recognition. Meanwhile, if there is a movement in the depth direction, a case where the movement is in the direction in which the slice moves and a case where the movement is in a direction opposite thereto have different influences on the results. However, although the movement being in the opposite direction to the slice movement direction results in the acquisition of redundant frames, there will at least be no oversight. This also provides the possibility to combine these frames to calculate cross-correlation between images having undergone binarization.

Figure 8F:
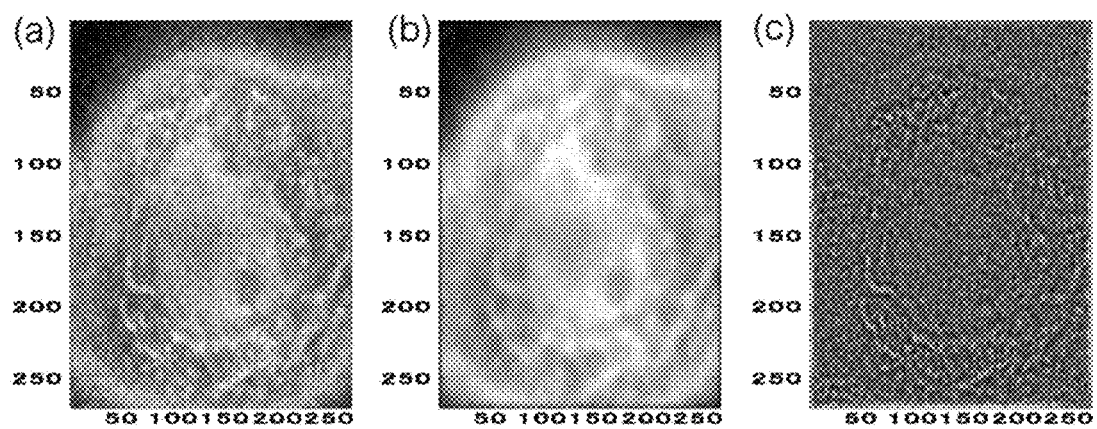
FIG. 8F(a) to FIG. 8F(c) illustrate filtering results of obtained image data.
Figure 8G:
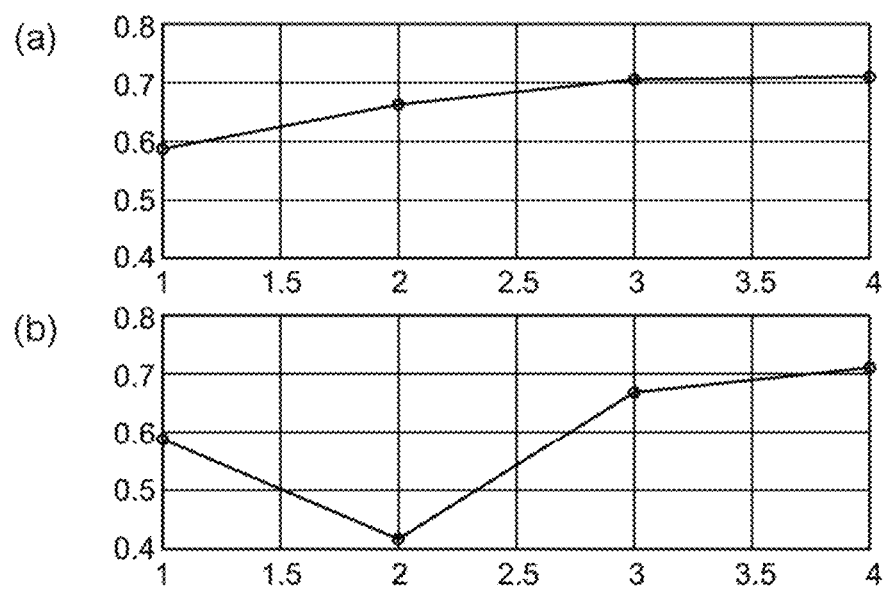
FIGS. 8G(a) and 8G(b) are diagrams, illustrating changes in a cross-correlation between frame images when a high-pass filter is applied.

As illustrated in FIG. 8F, based on a comparison between an image (b) obtained by applying a low-pass filter to an original image (a) and an image (c) obtained by applying a high-pass filter to the original image (a), it is anticipated that, for the correlation between the frames, application of the aforementioned cross-correlation calculation to the high-pass filtered image would demonstrate higher sensitivity to slice omissions. The result of applying same to the high-pass filtered image is illustrated in FIG. 8G. Prior to such cross-correlation calculation, a pre-process of extracting high space frequency components may be carried out to confirm lacking volume data.

In a different example, the site (segment) of a tissue in the breast interior may be identified on the basis of image data and the continuity may be determined on the basis of the geometric shape of the segment, thereby determining whether the breast has moved, for example. The segment may be, for example, water, mammary gland, fat, skin, Cooper's ligament, muscle, or the like. In addition to, or in place of, the geometric shape of the segment, the size of the segment and/or the number of appearance of the same type of segment may be used to determine whether the breast has moved and/or the degree of the movement.

Images of two consecutive frames or images of three or more consecutive frames may be used to determine the discontinuity. Furthermore, for the algorithm for continuity determination, a machine learning model such as a support vector machine (SVM) or deep learning may be employed. An advantageous method for combining the various motion detection indices having been described so far to carry out a comprehensive determination would be to use a cutting plane line (cutting plane: a N−1-dimensional surface in the case of N dimensions) determined through preliminary study to carry out identification in a multi-dimensional space corresponding to the number of indices. When the continuity of measured data is determined in this way, an imaging slice omission, or the like, can be detected and the precision of measurement for a test subject as a whole can be improved.

Figure 9A:
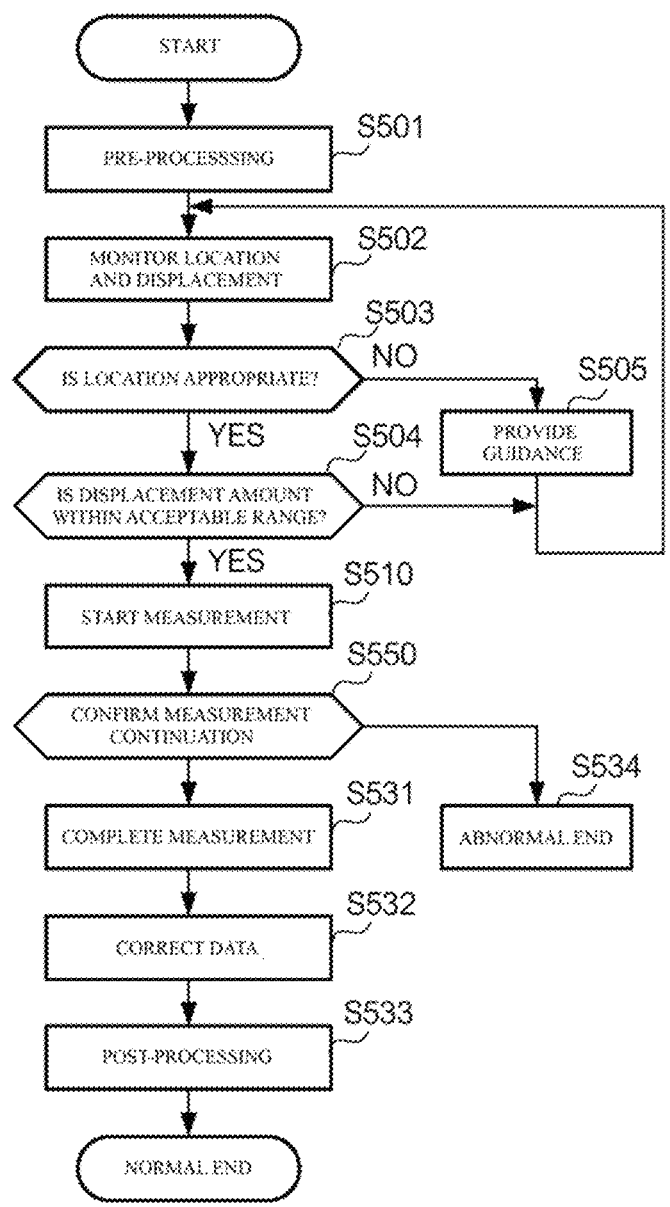
FIG. 9A is a flowchart, illustrating an example of operation of the ultrasonographic apparatus 100.
Figure 9B:
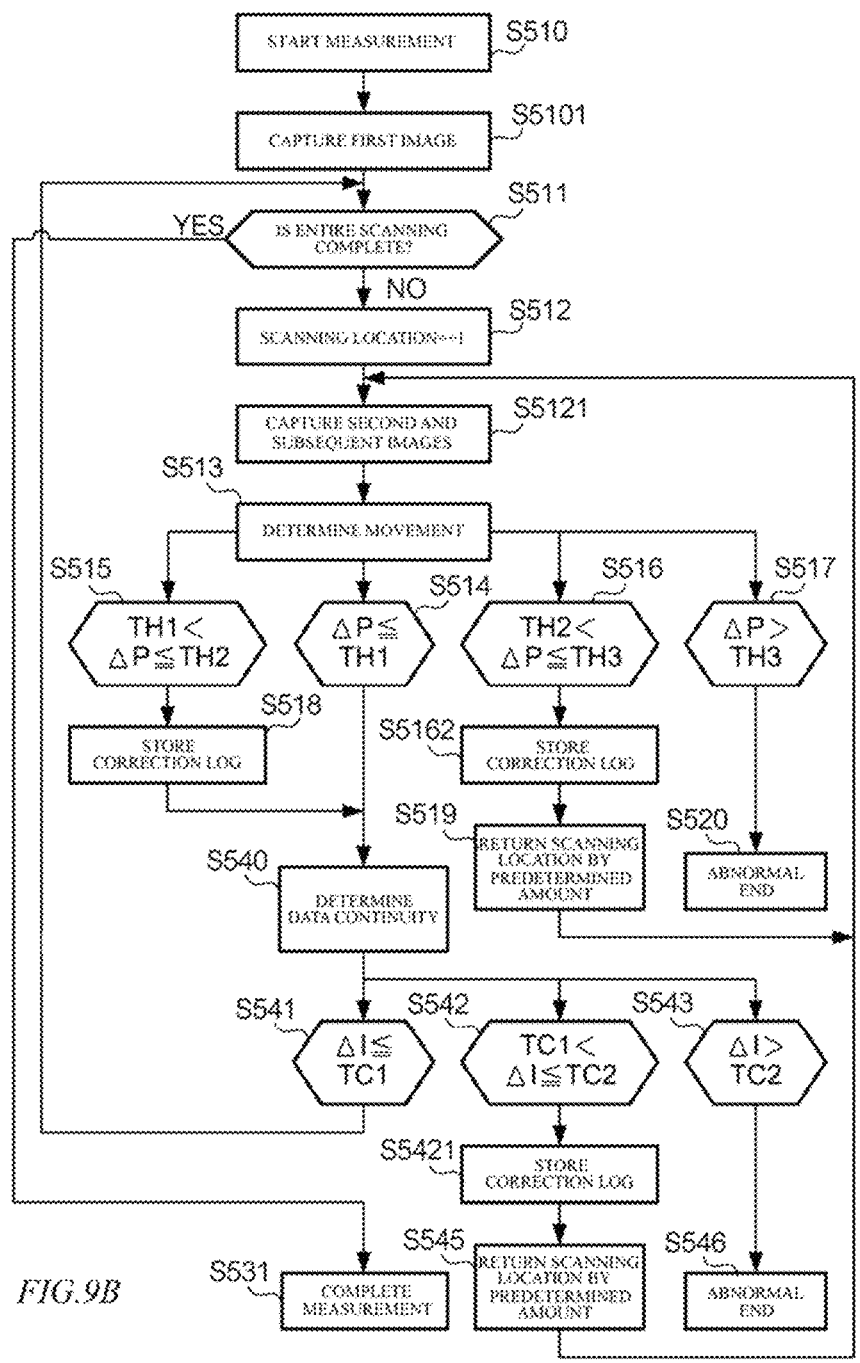
FIG. 9B is a flowchart, illustrating an example of operation of the ultrasonographic apparatus 100.

FIG. 9A and FIG. 9B are flowcharts presenting examples of the operation of the ultrasonographic apparatus 100. FIG. 9A illustrates an overall operation from before the start of measurement (preliminary stage) to the termination of the measurement, and FIG. 9B illustrates details of the operation during the data measurement from the start of the measurement to the termination (completion or abnormal end) of the measurement.

First, according to FIG. 9A, the human subject places a barcode in front of the reading device 940, for example, and allows the ultrasonographic apparatus 100 to recognize her/himself as a measurement target. At this time, the user information may also be read according to need, and the ultrasonographic apparatus 100 may set a parameter relating to the aforementioned acceptable range in accordance with the user information. Next, the ultrasonographic apparatus 100 carries out a pre-process, such as a water injection process, that is necessary for the measurement (S501).

Figure 10:
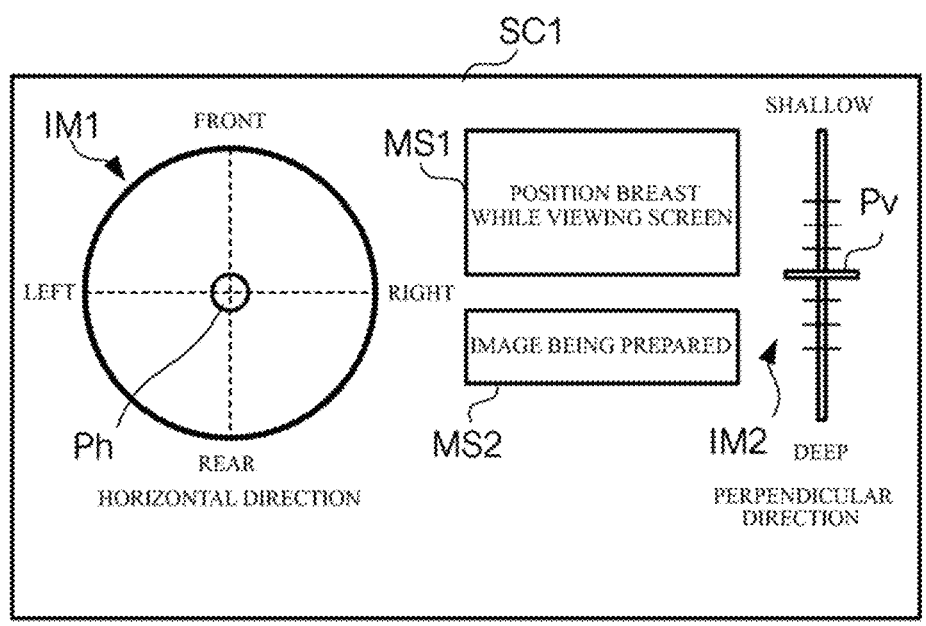
FIG. 10 is a diagram, illustrating examples of a screen that is displayed prior to start of measurement.

When the pre-process is complete, the human subject lies on the measurement table 910 with the face down and inserts one of the breasts as a test subject through the opening section 920. Then, the location detection unit 130 and the displacement measurement unit 140 start monitoring the location and displacement of the test subject (S502). FIG. 10 illustrates an example of a screen SC1 that is displayed on the touch panel 930 during the operation of the ultrasonographic apparatus 100. SC1 includes MS1, MS2, IM1, and IM2. In IM1, an image captured in real time by the camera 250 is displayed, and a reference location Ph and a guide line for assisting with positional alignment of the breast are also displayed in composited fashion. In IM2, the location of the breast in the depth direction detected by the ultrasonic element 230, and a reference location Pv and a guide memory for assisting with positional alignment in the depth direction are displayed. MS1 is a region in which guidance details are displayed, and MS2 is a region through which a measurement progress status is reported. The human subject adjusts the location and/or orientation of the body while looking at the screens in IM1 and IM2.

Referring back to FIG. 9A, the ultrasonographic apparatus 100 continues monitoring the location of the breast (S503, S504), and up to a time point at which it is confirmed that the breast is in an appropriate stationary state at an appropriate location (i.e. fluctuation (movement) of the location is within an acceptable range), provides guidance for assisting with the positional alignment (S505) according to need.

Figure 11A:
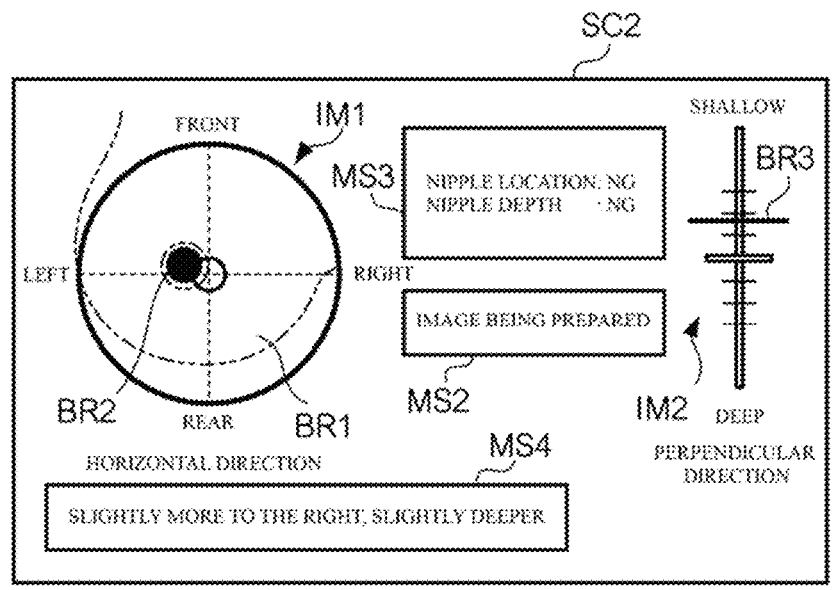
FIG. 11A and FIG. 11B are diagrams, illustrating an example of a screen that is displayed during measurement.
Figure 11B:
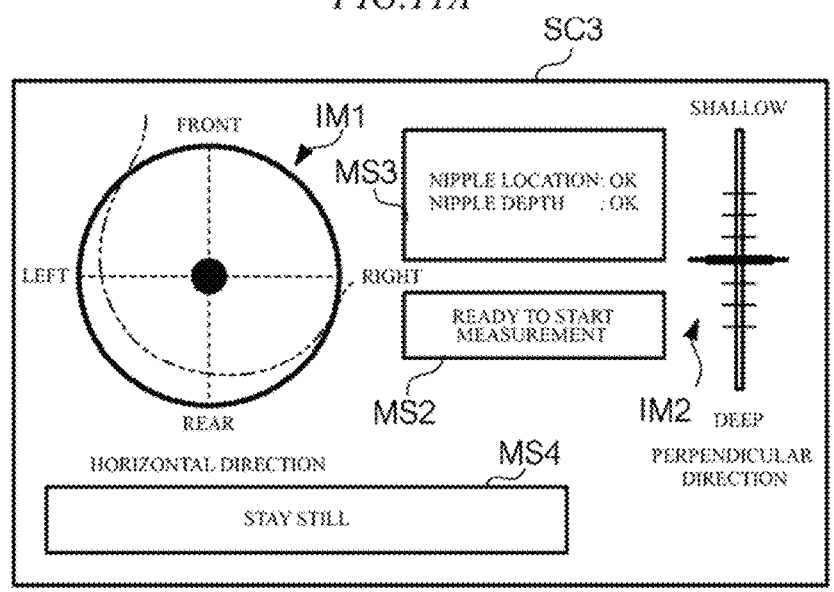

FIG. 11A and FIG. 11B illustrate examples of a screen SC2 in which the guidance is displayed and which is displayed prior to the start of the measurement. In IM1, a breast contour BR1 and a nipple BR2 as viewed in the perpendicular direction are displayed, and in IM2, a bar BR3 indicating the depth of the nipple is displayed. It is not necessary to display an unprocessed image captured by the camera 250, and image processing, such as emphasizing the contour and/or the nipple, which facilitates positional alignment by the human subject may be carried out.

MS3 is a region for reporting the location deviation state. In the example in FIG. 11A, the deviation of both the in-plane location and the depth location from the reference location is being reported. In MS4, a specific direction in which the breast is to be moved is displayed. When the human subject adjusts the location and the control unit 110 determines that the location is appropriate, then as shown in a screen SC3 illustrated in FIG. 11B, MS3 displays an indication that the location is appropriate and a message prompting to maintain the current state is displayed in MS4.

If the breast is at the appropriate location and movement of the breast is within an acceptable range, the ultrasonographic apparatus 100 determines that the conditions for starting measurement are satisfied and starts the measurement using the ring array 220. During the measurement, the ultrasonographic apparatus 100 monitors the location and movement of the breast (S550) and performs processes in accordance with the monitoring results. Specifically, if the location of the breast, movement of the breast, or continuity of the measured data during the measurement is within the acceptable range, the measurement is completed (S531). The ultrasonographic apparatus 100 makes a correction into the measured data according to need (S532), and carries out a post-process, such as drainage, (S533) to terminate the procedure. If the location or the movement is outside the acceptable range, the measurement is interrupted (S534). In this case, the ultrasonographic apparatus 100 may restart the measurement from the beginning by returning to S501, or the measurement for this human subject may be abandoned.

The process of S550 will now be described in detail with reference to FIG. 9B. First, the ultrasonographic apparatus 100 carries out the measurement at the initial location of the ring array 220 determined with reference to an in-body tissue, for example, and acquires a first image (image of a first frame) (S5101). Next, the ultrasonographic apparatus 100 updates the scanning location of the ring array 220 one step at a time (S512), and carries out ultrasonic measurement to acquire an image (S5121). Until completion of the measurement (S511), the ultrasonographic apparatus 100 continues monitoring the movement of the breast (S513) and also continues monitoring the continuity of the measured data (S540).

Specifically, the ultrasonographic apparatus 100 carries out processes in accordance with the degree of the movement of the breast (referred to as "body movement amount" below) (S513 to S519). Here, a case where ΔP is introduced as an index representing the body movement amount and TH1, TH2, and TH3 (TH1<TH2<TH3) are introduced as acceptable levels of ΔP will be described. When 0<ΔP≤TH1 (S514) stands, the state of the body movement is ideal, and subsequently, the continuity of the measured data is checked (S540).

Figure 12:
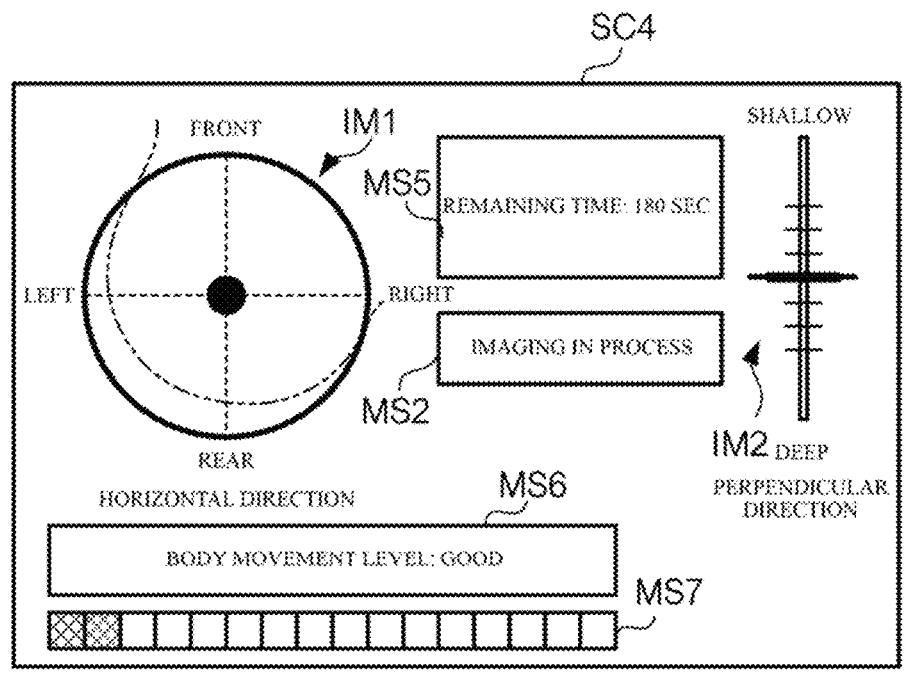
FIG. 12 is a diagram, illustrating an example of a screen that is displayed during measurement.

FIG. 12 illustrates an example of a screen SC4 that is displayed during the measurement. In MS6, the degree of the movement is displayed in text, and in MS7, the degree of the movement is displayed in a graph. In MS5, an expected time until termination of the measurement is displayed.

Referring back to FIG. 9B, when TH1<ΔP≤TH2 (S515) stands, the control unit 110 stores the current scanning location (the corresponding frame number; correction log) (S518) and continues the measurement. In this case, correction data relating to the stored frame number is created (S532) prior to the post-process (S533). At this time, in MS6 in FIG. 12, there may be displayed a message for prompting to reduce the body movement because the body movement is relatively large.

Referring back to FIG. 9B, when TH2<ΔP≤TH3 (S516) stands, the control unit 110 stores a correction log (S5162), returns the scanning location of the ring array 220 by a predetermined amount, and redoes part of the measurement (S519, 5121). At this time, in MS6 in FIG. 12, there may be displayed a massage for reducing the body movement because the body movement is considerably large, and it may also be reported that part of the measurement will be redone.

Referring back to FIG. 9B, if ΔP>TH3 (S517) stands, the body movement is beyond the acceptable range, so the control unit 110 interrupts the measurement (S520). The control unit 110 may return to S502 and automatically restart the measurement anew. Alternatively, the human subject may be prompted to choose between restarting the measurement anew and abandoning the measurement using the touch panel 930. The data having been measured up to this point may be discarded or saved in the storage unit 190. The current scanning location may be taken into consideration when determining to either discard or save the data. For example, if the current scanning location is deep (closer to the end of the measurement), it is highly probable that part of the data is usable, so the data may be saved, whereas if the current scanning location is shallow (closer to the beginning to the measurement), the entire data may be discarded.

Next, the ultrasonographic apparatus 100 carries out processes in accordance with the continuity of the data (S540 to S543). In S540, continuity between the data having the most recently acquired frame number and the data having the older frame numbers of 1 and above is determined. Here, an index of discontinuity is expressed by ΔI, and it is assumed that TC1 and TC2 (TC1<TC2) are set as acceptable levels of the discontinuity. A greater value of ΔI indicates an increase in the discontinuity (poorer continuity). When ΔI≤TC1 stands (S541), it is determined that the measurement has been carried out without any problem for the current frame, and the ring array is moved to the next scanning location (S512) to continue the measurement.

If TC1<ΔI≤TC2 stands (S542), data obtained in the current frame is estimated to be less reliable, so the data for this frame is deleted; then a correction log is stored (S5421), and the location of the ring array 220 is returned by a predetermined amount (S545) to carry out measurement (S5121).

If ΔI>TC2 stands (S543), the precision of the entire measurement is estimated to be less reliable, so the measurement is interrupted (S546).

When the entire scanning is completed (S511, YES), the measurement is completed (S531). If a frame to be corrected is registered in S518, the relevant data is corrected (S533). The image data, which has been corrected according to need, is stored in the storage unit 190 and is transferred to a data management server or the like, according to need.

If the other breast also is to be examined, the human subject is prompted to insert the other breast, and the processes in S501 to S533 are repeated.

According to this example, when the location of a breast and/or the degree of movement of the breast is inappropriate for performing measurement, a report to that effect is issued, and information for achieving a proper location and/or degree of movement is reported. Thus, accurate diagnostic images can be acquired independently of the skill of a medical personnel or other operator. Conceivable effects corresponding to the acquisition of accurate diagnostic images may include, inter alia, accurate determination of a site subject to imaging and/or the possibility to acquire complete imaging data with no omissions and/or a reduction in the instability of diagnostic precision dependent on the skill of a medical personnel or other operator in an image diagnosis, as well as other such effects. Furthermore, such information can be used for automatically completing the entire breast measurement. Moreover, when inputs are to be carried out by a human subject, the human subject can complete the measurement alone and there is no need for a medical personnel or other operator to be present during the measurement, so labor costs involved in the measurement can also be limited.

When the location of the breast and/or the degree of movement of the breast is inappropriate, measurement is not carried out or the measured data is not used, so precision of measurement results are guaranteed. Moreover, if the location and/or the degree of movement are within an acceptable range despite not being ideal, data can be corrected after the measurement or part of the measurement can be redone; in this way, the reliability of the data can be guaranteed and, moreover, time required for the measurement as a whole can be shortened compared to when the measurement is restarted from the beginning.

The obtained information relating to the results of determining the breast location and/or continuity may be used for setting parameters that are used in the process (calibration and/or rendering) of generating images from the ultrasonic measurement data. For example, when the same human subject carries out measurement next time, such information obtained during the measurement last time may be used to set a parameter to be used in image processing or a parameter relating to positional alignment. This information is found to reflect information peculiar to the human subject, such as the shape of the breast, state of breast internal tissue, and the like, so by using this information, measurement-related parameters can be set appropriately for each human subject. Moreover, when such information is obtained as a result of the same human subject performing measurement for both left and right breasts, information on both breasts can be compared and used in the diagnosis.

In addition, according to the examples above, biological data relating to the state of the interior of the entire breast under measurement can be linked with information representing the location of other in-body tissues such as ribs and information on the degree of continuity (or discontinuity) of the biological data across the entire target site can be recorded. For organs that constitute a left and right pair, such as the breasts, in particular, measurement data obtained for both left and right organs can be compared, or changes observed over time in the results of comparing a plurality of measurements carried out periodically can be accumulated, and thus data that can be effectively used in performing a diagnosis or a follow-up after surgery can be obtained.

Other Examples

In the present invention, the scanning direction of the ring array 220 does not have to be linear. When, for example, the ring array 220 is formed from a probe having a C-shape or a halved ring shape, or from a linear probe in which a set of opposing linear elements are provided, both scanning in a horizontal plane (rotating motion) and scanning in a perpendicular direction (upward motion or downward motion) are required. In cases like this, a spiral motion or other such three-dimensional motion that has a constantly changing movement direction may be performed. In this case, the amount by which the location of the ring array 220 is to be returned may be defined as a length on the movement path of the ring array 220. Further, the present invention is also applicable to a measurement mode in which scanning is performed two-dimensionally in a horizontal plane to obtain data on the entire region of a subject. Accordingly, the orientation of a breast during measurement is not limited to a vertical orientation (breast being hung).

An arbitrary number of levels, which is larger than or equal to four levels, may be set for the continuity of data or the acceptability relating to the movement of the breast. Moreover, even when part of measurement is to be redone, the point to which the process is to be returned may be determined according to the level of the continuity of the data or the acceptability relating to the movement of the breast. For example, when it is intended to increase the precision in conformity with an increase in the movement despite the degree of movement being within the acceptable range, it is conceivable to return to an even earlier scanning location (older frame) to carry out the measurement or data correction so as to increase the amount of data to be re-measured. To present an example, in S516 (TH2<ΔP≤TH3), a threshold (THa) is further set such that TH2<THa<TH3 is satisfied, and when the movement exceeds the acceptable range at the scanning location z=z1, the ring array is returned by Δz1 from the scanning location z=z1 if TH2<ΔP≤THa stands, whereas the ring array is returned by Δz2(>Δz1) from z=z1 if THa<ΔP≤TH3 stands.

Alternatively, details of data correction may be changed according to the degree of the continuity of the data and/or the degree of deviation in the location. For example, a threshold (THb) is set such that TH1<THb<TH2 is satisfied, and a correction algorithm A for which the correction precision is lower but calculation time is shorter and a correction algorithm B for which the correction precision is higher but calculation time is longer are prepared; the correction algorithm A is applied when TH1<ΔP<THb stands, whereas the correction algorithm B is applied when THb<ΔP<TH2 stands. In this way, by changing the point from which to redo the measurement and/or changing the details of data correction post-processing in accordance with the degree of the continuity (or discontinuity) of the data and/or the degree of deviation in the location, it is possible to both guarantee measurement precision and shortening the measurement time.

The method for setting an acceptability relating to the degree of the continuity of the data and the degree of deviation in the location and the method for determining the point from which to redo the measurement and the data correction post-processing may be determined in consideration of the purpose of examination, symptom, a preset time limitation, preferences by a human subject, and so on. For example, it is conceivable to set a tighter acceptable degree for a human subject who can afford to repeat the measurement a few times (spend more time) and desires higher precision in the measurement, whereas to set a looser acceptable range for a human subject who has difficulty in staying still. Such information may be incorporated as human subject attributes and read by the ultrasonographic apparatus 100 together with identification information for the human subject before measurement.

In other words, an ultrasonographic apparatus of the present invention may at least include a measurement device including an ultrasonic element group configured to emit an ultrasonic wave into the bath tank and receive the ultrasonic wave having been scattered, and a control unit configured to carry out measurement by the ultrasonic element group in a case in which at least one from among a three-dimensional location of the breast and continuity of data measured by the measurement device satisfies a predetermined condition.

Although the embodiments above describe a breast of a body as a representative example of a test subject, the apparatus and method of the present invention can also be applied to the measurement of a test subject constituting a different part of the body of a human subject from a breast of the body.

Moreover, although the embodiments above describe an ultrasonographic apparatus as a medical imaging apparatus, the present invention can also be applied to medical imaging apparatuses employing other measurement techniques than ultrasonic measurement (e.g. microwave diagnostic apparatus, photoacoustic diagnostic apparatus, positron emission tomography (PET) apparatus, etc.). In other words, even when the measurement device used in the present invention includes, in place of the aforementioned ultrasonic element group, an element group configured to emit and receive a different form of radiation waves, the location of a test subject may be detected or monitored using the aforementioned location detection ultrasonic element, for example, and control may be performed such that in a case in which at least one from among the location, a change over time in the location, and continuity of data measured by the device satisfies a predetermined condition, measurement using the device is carried out. This location may be a three-dimensional location expressed by an orthogonal coordinate system or a polar coordinate system, or may be a two-dimensional or one-dimensional location if there are limitations on the freedom of the location and/or movement.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

DESCRIPTION OF REFERENCE NUMERALS AND SYMBOLS 100 an ultrasonographic apparatus (medical imaging apparatus)
920 an opening section
930 a touch panel (report unit)
940 a reading device
950 microphone/speaker
910 a measurement table
200 a measurement module
210 a bath tank
220 a ring array (measuring device)
230 an ultrasonic element (ultrasonic element for location detection)
240 a support member
250 a camera
241 a moving mechanism
960 a pressure sensor
130 location detection unit
131 first location detection unit
132 second location detection unit
140 displacement measurement unit
141 first displacement measurement unit
142 second displacement measurement unit
190 storage unit
150 data processing unit
151 continuity determination unit
152 data correction unit
161 drive unit
163 information input unit
170 report unit
171 display unit
172 sound output unit

The invention claimed is:

1. A medical imaging apparatus comprising:
a bath tank for accommodating a test subject, the test subject being at least a portion of a body of a human subject;
a measurement device, for measuring the test subject, automatically movable in a predetermined direction, the measurement device including a group of ultrasonic elements for measurement to emit an ultrasonic wave into the bath tank and receive a scattered ultrasonic wave;
a control unit for measuring by the measurement device when from among a location of the test subject within a plane orthogonal to the predetermined direction, a location of the test subject in the predetermined direction, and continuity of data measured by the measurement device satisfies a predetermined condition,
wherein if it is determined that degree of deviation in the location of the test subject or discontinuity of the data measured at time of measurement does not satisfy the predetermined condition, the control unit performs any of: a processing in which the measurement is continued and the measured data is corrected; a processing in which the location of the measurement device in a movement direction is returned by a predetermined distance and a part of the measurement is redone; and a processing in which the measurement is restarted from beginning,
the process in which the measurement is continued and the measured data is corrected is performed if it is determined that the degree of deviation in the location of the test subject or the discontinuity of the measured data exceeds a first acceptable range serving as the predetermined condition,
the process in which the location of the measurement device in the movement direction is returned by the predetermined distance and the part of the measurement is redone is performed if it is determined that the degree of deviation in the location of the test subject or the discontinuity of the measured data exceeds a second acceptable range serving as the predetermined condition, and
the process in which the measurement is restarted from the beginning is performed if it is determined that the degree of deviation in the location of the test subject or the discontinuity of the measured data exceeds a third acceptable range serving as the predetermined condition, and
wherein the second acceptable range is greater than the first acceptable range and the third acceptable range is greater than the second acceptable range; and
a location detection unit for detecting the location of the test subject in the bath tank within the plane orthogonal to the predetermined direction and/or the location of the test subject in the bath tank in the predetermined direction,
wherein the control unit determines the location of the test subject by the location detection unit on the basis of a location of an in-body tissue located on the opposite side from a region subject to measurement by the measurement device relative to an initial location where the measurement device starts measurement or a termination location where the measurement device terminates measurement,
the location detection unit comprises a location detection ultrasonic element which is constituted by a group of elements differing from the group of ultrasonic elements for measurement and located on the bottom surface of the bath tank.

2. The medical imaging apparatus according to claim 1, wherein the control unit determines the initial location where the measurement device starts measurement and/or the termination location where the measurement device terminates measurement, on the basis of the location of a predetermined in-body tissue of the human subject.

3. The medical imaging apparatus according to claim 1, wherein the test subject is a breast of the human subject and the in-body tissue is a rib, chest wall, or pectoralis major muscle of the human subject.

4. The medical imaging apparatus according to claim 1, wherein the location detection unit comprises:
- a first location detection unit for detecting the location of the test subject within the plane orthogonal to the predetermined direction; and
- a second location detection unit for detecting the location of the test subject in the predetermined direction, and
- at least one of the first location detection unit and the second location detection unit is comprised of the location detection ultrasonic element.

5. The medical imaging apparatus according to claim 1, wherein, if the measured location of the test subject is within a predetermined range, the control unit starts a processing for measuring data continuously while moving the measurement device in the predetermined direction.

6. A medical imaging apparatus comprising:
- a bath tank for accommodating a test subject, the test subject being at least a portion of a body of a human subject;
- a measurement device, for measuring the test subject, movable in a predetermined direction, the measurement device including a group of elements to emit an ultrasonic wave into the bath tank and receive a scattered ultrasonic wave; and
- a control unit for measuring by the measurement device when from among a location of the test subject within a plane orthogonal to the predetermined direction, a location of the test subject in the predetermined direction, and continuity of data measured by the measurement device, at least the location of the test subject in the predetermined direction and the continuity of the data measured by the measurement device satisfy a predetermined condition,
- wherein if it is determined that degree of deviation in the location of the test subject or discontinuity of the data measured at time of measurement does not satisfy the predetermined condition, the control unit performs any of: a processing in which the measurement is continued and the measured data is corrected; a processing in which the location of the measurement device in a movement direction is returned by a predetermined distance and a part of the measurement is redone; and a processing in which the measurement is restarted from beginning,
- the process in which the measurement is continued and the measured data is corrected is performed if it is determined that the degree of deviation in the location of the test subject or the discontinuity of the measured data exceeds a first acceptable range serving as the predetermined condition,
- the process in which the location of the measurement device in the movement direction is returned by the predetermined distance and the part of the measurement is redone is performed if it is determined that the degree of deviation in the location of the test subject or the discontinuity of the measured data exceeds a second acceptable range serving as the predetermined condition, and
- the process in which the measurement is restarted from the beginning is performed if it is determined that the degree of deviation in the location of the test subject or the discontinuity of the measured data exceeds a third acceptable range serving as the predetermined condition, and
- wherein the second acceptable range is greater than the first acceptable range and the third acceptable range is greater than the second acceptable range.

7. A non-transitory, computer-readable medium storing one or more instructions executable by a computer system of a medical imaging apparatus to perform operations, the medical imaging apparatus comprising:
- a bath tank for accommodating a test subject, the test subject being at least a portion of a body of a human subject; and
- a measurement device, for measuring the test subject, movable in a predetermined direction, the measurement device including a group of elements to emit an ultrasonic wave into the bath tank and receive a scattered ultrasonic wave;

the operations comprising:
- determining whether, from among a location of the test subject within a plane orthogonal to the predetermined direction, a location of the test subject in the predetermined direction, and continuity of data measured by the measurement device, at least the location of the test subject in the predetermined direction and the continuity of the data measured by the measurement device satisfy a predetermined condition,
- using a result of the determination to determine whether to perform measurement by the measurement device, and
- if it is determined that degree of deviation in the location of the test subject or discontinuity of the data measured at time of measurement does not satisfy the predetermined condition, performing any of: a processing in which the measurement is continued and the measured data is corrected; a processing in which the location of the measurement device in a movement direction is returned by a predetermined distance and a part of the measurement is redone; and a processing in which the measurement is restarted from beginning, wherein
- the process in which the measurement is continued and the measured data is corrected is performed if it is determined that the degree of deviation in the location of the test subject or the discontinuity of the measured data exceeds a first acceptable range serving as the predetermined condition,
- the process in which the location of the measurement device in the movement direction is returned by the predetermined distance and the part of the measurement is redone is performed if it is determined that the degree of deviation in the location of the test subject or the discontinuity of the measured data exceeds a second acceptable range serving as the predetermined condition, and
- the process in which the measurement is restarted from the beginning is performed if it is determined that the degree of deviation in the location of the test subject or the discontinuity of the measured data exceeds a third acceptable range serving as the predetermined condition, and
- wherein the second acceptable range is greater than the first acceptable range and the third acceptable range is greater than the second acceptable range.

8. The medical imaging apparatus according to claim 1, wherein the control unit detects slice omissions to determine discontinuity of data within the measured data.

* * * * *

UNITED STATES PATENT AND TRADEMARK OFFICE
CERTIFICATE OF CORRECTION

PATENT NO. : 11,517,284 B2
APPLICATION NO. : 16/652249
DATED : December 6, 2022
INVENTOR(S) : Mika Seki et al.

Page 1 of 1

It is certified that error appears in the above-identified patent and that said Letters Patent is hereby corrected as shown below:

On the Title Page

Item [54], delete "BANK" and insert -- BATH --

In the Specification

Column 1, Line 2, delete "BANK" and insert -- BATH --

Signed and Sealed this
Twenty-fourth Day of January, 2023

Katherine Kelly Vidal
*Director of the United States Patent and Trademark Office*